(12) United States Patent
Bar-On et al.

(10) Patent No.: US 10,035,005 B2
(45) Date of Patent: Jul. 31, 2018

(54) DEVICES FOR URETHRAL TREATMENT

(75) Inventors: Raz Bar-On, Hadera (IL); Roni Shabat, Kfar Yehezkel (IL); Shai Golan, Kibbutz Megiddo (IL); Yoav Lengel, Ramat-HaSharon (IL); Yair Feld, Haifa (IL)

(73) Assignee: ProArc Medical Ltd., Misgav Business Park (IL)

( * ) Notice: Subject to any disclaimer, the term of this patent is extended or adjusted under 35 U.S.C. 154(b) by 232 days.

(21) Appl. No.: 14/005,330

(22) PCT Filed: Mar. 15, 2012

(86) PCT No.: PCT/IL2012/050094
§ 371 (c)(1),
(2), (4) Date: Sep. 16, 2013

(87) PCT Pub. No.: WO2012/123950
PCT Pub. Date: Sep. 20, 2012

(65) Prior Publication Data
US 2014/0012192 A1   Jan. 9, 2014

Related U.S. Application Data

(60) Provisional application No. 61/569,837, filed on Dec. 13, 2011, provisional application No. 61/453,652, filed on Mar. 17, 2011.

(51) Int. Cl.
*A61M 29/00* (2006.01)
*A61M 29/02* (2006.01)
(Continued)

(52) U.S. Cl.
CPC .......... *A61M 29/02* (2013.01); *A61B 17/083* (2013.01); *A61B 17/32* (2013.01);
(Continued)

(58) Field of Classification Search
CPC .............. A61M 29/02; A61M 229/025; A61M 2029/025; A61B 17/32; A61B 17/083;
(Continued)

(56) References Cited

U.S. PATENT DOCUMENTS 4,660,560 A   4/1987   Klein
5,030,227 A   7/1991   Rosenbluth et al.
(Continued)

FOREIGN PATENT DOCUMENTS

EP   0125352   11/1984
EP   1413262   4/2004
(Continued)

OTHER PUBLICATIONS

Official Action dated Mar. 16, 2015 From the US Patent and Trademark Office Re. U.S. Appl. No. 13/257,651.
(Continued)

*Primary Examiner* — Christopher D Prone
*Assistant Examiner* — Rokhaya Diop

(57) ABSTRACT

A dilation device (206) for an intra-body lumen, for example, a urethra partially occluded by an enlarged prostate in the form of a resilient curved body configured to be implanted in a cut around the lumen, and a method for dilating such a lumen by implanting a dilation device in a cut around the outside of the lumen. Also, a deployment system (300) including a delivery device for the implant, and a device for dilating the lumen before and while the cut is being made, and a method of using the implant and the deployment system. The implant may be formed of a strip or a coiled wire. The cut may be performed in part by the implant. The cut may be performed by a sharp edge, and/or by application of electrical current to the area being cut, or by a piezoelectric transducer.

23 Claims, 17 Drawing Sheets

(51) Int. Cl.
*A61F 2/04* (2013.01)
*A61B 17/08* (2006.01)
*A61B 17/3205* (2006.01)
*A61B 17/3209* (2006.01)
*A61F 2/958* (2013.01)
*A61B 17/00* (2006.01)
*A61B 17/32* (2006.01)

(52) U.S. Cl.
CPC ...... *A61B 17/3205* (2013.01); *A61B 17/3209* (2013.01); *A61F 2/04* (2013.01); *A61B 2017/00274* (2013.01); *A61B 2017/320044* (2013.01); *A61F 2/958* (2013.01); *A61F 2002/047* (2013.01); *F04C 2270/0421* (2013.01)

(58) Field of Classification Search
CPC ............ A61B 17/3205; A61B 17/3209; A61B 2017/00274; A61B 2017/320044; A61F 2/04; A61F 2002/047; A61F 2002/048; A61F 2002/048; A61F 2/958; F04C 2270/0421
See application file for complete search history.

(56) References Cited

U.S. PATENT DOCUMENTS

| | | | |
|---|---|---|---|
| 5,269,802 | A | 12/1993 | Garber |
| 5,674,242 | A | 10/1997 | Phan et al. |
| 5,766,203 | A | 6/1998 | Imran et al. |
| 6,070,589 | A | 6/2000 | Keith et al. |
| 6,319,282 | B1 | 11/2001 | Nishi |
| 7,004,965 | B2 | 2/2006 | Gross |
| 7,632,297 | B2 | 12/2009 | Gross |
| 8,016,845 | B1* | 9/2011 | Sauer ............. A61B 17/320016 604/22 |
| 2002/0007222 | A1 | 1/2002 | Desai |
| 2002/0032486 | A1 | 3/2002 | Lazarovitz et al. |
| 2002/0032488 | A1 | 3/2002 | Brekke et al. |
| 2002/0035391 | A1 | 3/2002 | Mikus et al. |
| 2003/0060870 | A1 | 3/2003 | Reever |
| 2003/0069467 | A1 | 4/2003 | Desmond, III et al. |
| 2003/0167088 | A1 | 9/2003 | Abraham et al. |
| 2003/0191479 | A1* | 10/2003 | Thornton ........... A61B 17/0644 606/151 |
| 2003/0216814 | A1 | 11/2003 | Siegel et al. |
| 2004/0030217 | A1 | 2/2004 | Yeung et al. |
| 2004/0064139 | A1* | 4/2004 | Yossepowitch A61B 17/320016 606/46 |
| 2004/0181235 | A1 | 9/2004 | Daignault et al. |
| 2005/0055087 | A1 | 3/2005 | Starksen |
| 2005/0137716 | A1 | 6/2005 | Gross |
| 2006/0167540 | A1* | 7/2006 | Masters ................... A61F 2/90 623/1.44 |
| 2006/0276871 | A1 | 12/2006 | Lamson et al. |
| 2009/0156977 | A1 | 6/2009 | Daignault et al. |
| 2009/0264987 | A1 | 10/2009 | Gale |
| 2010/0130815 | A1* | 5/2010 | Gross ....................... A61F 2/92 600/30 |
| 2010/0137893 | A1 | 6/2010 | Kilemnick et al. |
| 2010/0292715 | A1 | 11/2010 | Nering et al. |
| 2012/0010645 | A1 | 1/2012 | Feld |
| 2016/0000455 | A1 | 1/2016 | Golan et al. |
| 2016/0096009 | A1 | 4/2016 | Feld |

FOREIGN PATENT DOCUMENTS

| | | |
|---|---|---|
| JP | 2004-147812 | 5/2004 |
| WO | WO 01/43664 | 6/2001 |
| WO | WO 2007/048437 | 5/2007 |
| WO | WO 2007/109621 | 9/2007 |
| WO | WO 2008/056194 | 5/2008 |
| WO | WO 2008/142677 | 11/2008 |
| WO | WO 2010/106543 | 9/2010 |
| WO | WO 2012/123950 | 9/2012 |
| WO | WO 2014/141278 | 9/2014 |

OTHER PUBLICATIONS

Restriction Official Action dated Apr. 22, 2014 From the US Patent and Trademark Office Re. U.S. Appl. No. 13/257,651.
International Search Report and the Written Opinion dated Jul. 3, 2014 From the International Searching Authority Re. Application No. PCT/IL2014/050281.
Official Action dated Aug. 12, 2014 From the US Patent and Trademark Office Re. U.S. Appl. No. 13/257,651.
Communication Relating to the Results of the Partial International Search dated Jul. 4, 2012 From the International Searching Authority Re. Application No. PCT/IL2012/050094.
Communication Relating to the Results of the Partial International Search dated Nov. 8, 2010 From the International Searching Authority Re. Application No. PCT/IL2010/000229.
International Preliminary Report on Patentability dated Sep. 29, 2011 From the International Bureau of WIPO Re. Application No. PCT/IL2010/000229.
International Search Report and the Written Opinion dated Sep. 13, 2012 From the International Searching Authority Re. Application No. PCT/IL2012/050094.
International Search Report and the Written Opinion dated Jan. 18, 2011 From the International Searching Authority Re. Application No. PCT/IL2010/000229.
Rectification of Obvious Mistake Under Rule 91.1. dated Jul. 6, 2010 From the International Searching Authority of the European Patent Office Re. Application No. PCT/IL2010/000229.
International Preliminary Report on Patentability dated Sep. 24, 2015 From the International Bureau of WIPO Re. Application No. PCT/IL2014/050281.
Official Action dated Sep. 15, 2015 From the US Patent and Trademark Office Re. U.S. Appl. No. 13/257,651.
International Preliminary Report on Patentability dated Sep. 26, 2013 From the International Bureau of WIPO Re. Application No. PCT/IL2012/050094.
Communication Pursuant to Article 94(3) EPC dated Sep. 24, 2014 From the European Patent Office Re. Application No. 12716658.5.
Communication Pursuant to Article 94(3) EPC dated Mar. 23, 2016 From the European Patent Office Re. Application No. 12716658.5.
Official Action dated Mar. 24, 2016 From the US Patent and Trademark Office Re. U.S. Appl. No. 13/257,651.
Official Action dated Sep. 9, 2016 From the US Patent and Trademark Office Re. U.S. Appl. No. 13/257,651.
Supplementary European Search Report and the European Search Opinion dated Oct. 28, 2016 From the European Patent Office Re. Application No. 14764625.1.
Communication Pursuant to Article 94(3) EPC dated Feb. 21, 2017 From the European Patent Office Re. Application No. 10714484.2. (4 Pages).
Official Action dated Apr. 19, 2017 From the US Patent and Trademark Office Re. U.S. Appl. No. 13/257,651. (26 pages).
Official Action dated Sep. 8, 2017 From the US Patent and Trademark Office Re. U.S. Appl. No. 13/257,651. (19 pages).
Applicant-Initiated Interview Summary dated Jan. 16, 2018 From the US Patent and Trademark Office Re. U.S. Appl. No. 13/257,651. (3 pages).
Restriction Official Action dated Nov. 30, 2017 From the US Patent and Trademark Office Re. U.S. Appl. No. 14/967,308. (8 pages).

* cited by examiner

FIG. 2A
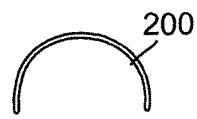
FIG. 2B
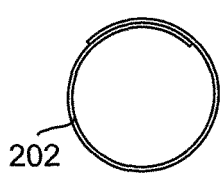
FIG. 2C
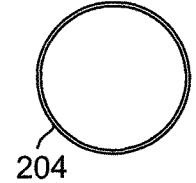
FIG. 2D
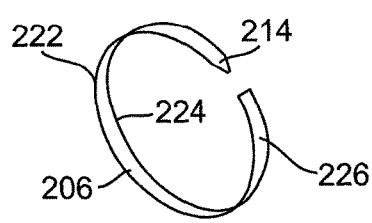
FIG. 2E
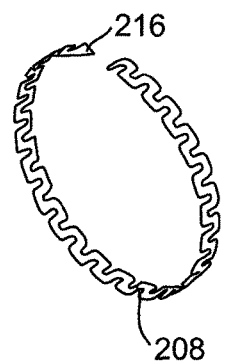
FIG. 2F
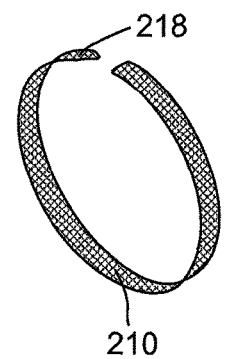
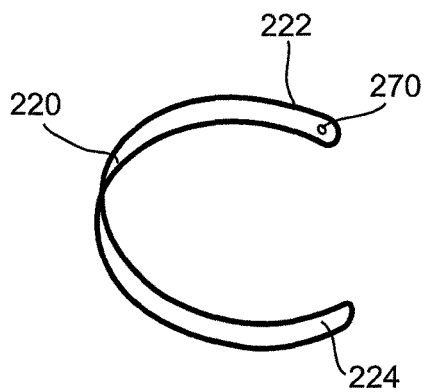
FIG. 2G

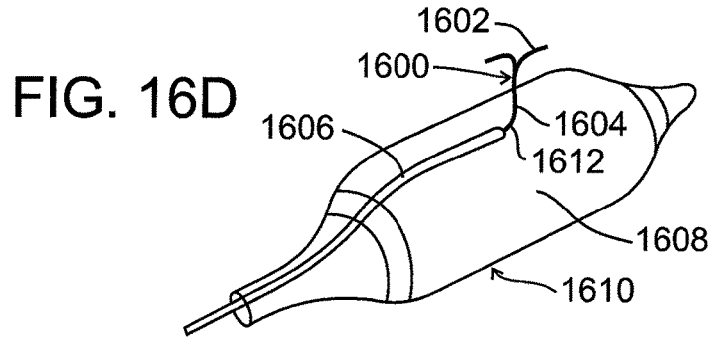
FIG. 16D
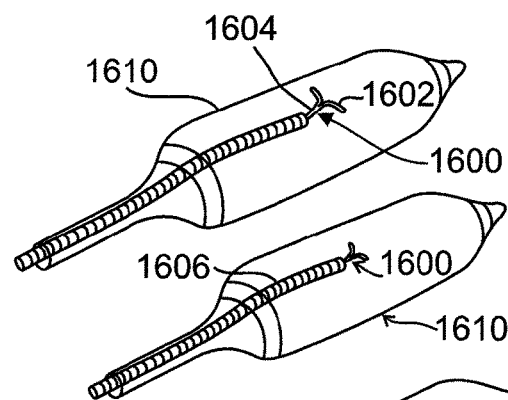
FIG. 16C
FIG. 16B
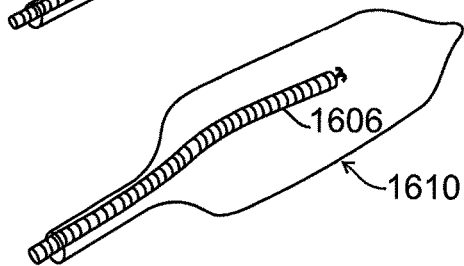
FIG. 16A
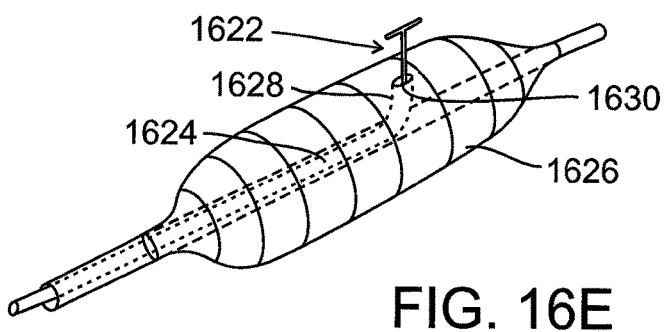
FIG. 16E

DEVICES FOR URETHRAL TREATMENT

RELATED APPLICATIONS

This application is a National Phase of PCT Patent Application No. PCT/IL2012/050094 having International filing date of Mar. 15, 2012, which claims the benefit of priority under 35 USC § 119(e) of U.S. Provisional Patent Application No. 61/569,837 filed on Dec. 13, 2011 and 61/453,652 filed on Mar. 17, 2011.

This application is also related to U.S. patent application Ser. No. 13/257,651 filed Mar. 21, 2010, which is a National Phase of PCT Patent Application No. PCT/IL2010/000229 filed Mar. 21, 2010 and published as WO2010/106543 on Sep. 23, 2010.

The contents of the above-identified applications are incorporated by reference herein as if fully set forth.

FIELD OF THE INVENTION

The present invention, in some of its embodiments, relates to devices and methods for treatment of intra-body lumens, and, more particularly, but not exclusively, to devices and methods for dilating and/or assisting in dilation and/or maintaining dilation of the urethra to relieve obstruction resulting, for example from benign prostatic hyperplasia (BPH).

BACKGROUND OF THE INVENTION

It is common for the prostate gland to become enlarged as a man ages. As a male matures, the prostate goes through two main periods of growth, first early in puberty, and then again at around age 25, when the growth begins, and continues on through life. One of the effects of this continued growth can be pressure on the urethra, the passage through which urine passes from the bladder and the penis.

The urethra is surrounded by the prostate for part of its length. Within the confines of the prostate, the urine flows through a passage having a generally triangular cross-section. As the prostate enlarges, the layer of tissue surrounding the prostate restricts the prostate from expanding outward, causing the prostate to constrict the urethral passage. The condition of an enlarged, non-cancerous prostate is called benign prostatic hyperplasia (BPH), or benign prostatic hypertrophy.

Though the prostate continues to grow during most of a man's life, BPH rarely causes symptoms before age 40, but more than half of men in their sixties and as many as 90 percent in their seventies and eighties have some symptoms of BPH. BPH can make it difficult to the bladder to completely empty, and is associated with other urinary system problems well known in the medical field.

Current Treatment

Men who have BPH with symptoms usually need some kind of treatment at some time. Although the need for treatment is not usually urgent, doctors generally advise treatment once the problems become bothersome or present a health risk.

The most commonly used treatments for BPH include drug therapy, minimally invasive mechanical treatment, and surgery.

Among the drugs approved for example, by the U.S. FDA, are Finasteride (Proscar), dutasteride (Avodart), terazosin (Hytrin), doxazosin (Cardura), tamsulosin (Flomax), and alfuzosin (Uroxatral). These drugs act by relaxing the smooth muscle of the prostate and bladder neck to improve urine flow and to reduce bladder outlet obstruction. Use of finasteride and doxazosin together has also been found to be more effective than using either drug.

Drug treatment may only be partially effective in some cases. Researchers have therefore developed a number of mechanical procedures that relieve BPH symptoms but are less invasive than conventional surgery. These include transurethral microwave thermotherapy (TUMT), which uses microwaves to heat and destroy portions of prostate tissue, transurethral needle ablation (TUNA), which employs low-level radio-frequency energy delivered through twin needles to burn away selected regions of the enlarged prostate, and water-induced thermotherapy, which uses heated water to destroy portions of prostate tissue. The use of ultrasound waves to destroy prostate tissue is also undergoing clinical trials in the United States.

Urethral stents have also been employed in some instances, with varying degrees of effectiveness, but also exhibit some drawbacks in some cases, known in the art. These include pain and/or irritation, frequent urination and/or incontinence, and difficulty in removal (which proves to be necessary in one-third of cases).

Surgical removal of part of the prostate, thereby reducing pressure against the urethra is often regarded as the best long-term solution for patients with BPH. Among the types of surgery commonly employed is transurethral surgery which requires no external incision. Such procedures include transurethral resection of the prostate (TURP), by which prostate tissue is removed, transurethral incision of the prostate (TUIP), by which the urethra is widened by making a few small cuts in the bladder neck where the urethra joins the bladder, and in the prostate gland itself, and laser induced prostate tissue removal.

In the few cases where transurethral surgical procedures are not indicated, open surgery, which requires an external incision, may be used.

WO/2010/106543 referred to above, provides mechanical alternatives and methods to current non-surgical treatments for BPH.

Of general interest may be Gross et al. U.S. patent publication 2010/0130815, which is concerned with implantation of devices to provide pre-operative urethral expansion.

SUMMARY OF THE INVENTION

The present invention, in some of its embodiments, provides mechanical alternatives and alternative methods to current non-surgical treatments for a constricted bodily lumen, for example, a urethra constricted due to BPH.

According to an aspect of some embodiments of the present invention there is provided an implant for deployment in an intra-body lumen to dilate the lumen, for example, a constricted portion of a urethra, the implant being formed by a resilient body configured for deployment in a peripheral cut formed around the lumen, for example, in an enlarged prostate, wherein the implant is configured to be delivered to the deployment site in a compressed condition, and is releasable to at least a partially uncompressed condition after delivery.

Optionally, the implant is configured to at least partially fill the base of a cut formed in the lumen.

Optionally, a portion of the implant is coated by a dielectric material.

Optionally, the implant is configured to be only partially relaxed upon deployment, whereby it applies a radial force in the cut to enable further post-deployment dilation.

According to an aspect of some embodiments of the present invention, the implant is configured as a substantially flat surfaced C-shaped open ring, a spiral ring, a helical ring, or a closed ring or a wire, the length of which is selected according to the lumen to be dilated.

Optionally, the implant has protrusions on its longitudinal edges.

Optionally, the implant has protrusions on a flat surface thereof.

Optionally, the implant is formed of nitinol, stainless steel, or chromium-cobalt, or a biodegradable or other biocompatible material.

According to an aspect of some embodiments of the present invention the implant carries a drug which is released after deployment.

Optionally, the length of the implant is determined by the lumen to be dilated by the implant.

Optionally, the width of the implant is in the range of about 0.1 mm to about 10 mm and in the range of about 0.05 mm to about 0.5 mm thick.

Optionally, the implant is a wire coil having a diameter in the range of about 0.1 mm up to about 10 mm and the wire has a diameter of 0.01 mm or more.

According to an aspect of some embodiments of the present invention, there is provided a device for deployment of an implant to dilate a bodily lumen, for example, a urethra, having an elongated shaft, a cutter attached distally to the shaft to form a cut into a surrounding tissue, for example the prostate for receiving an implant, a dilation device for expanding the urethra during an implantation procedure, and a release mechanism for an implant.

Optionally, the device is configured for delivery of the implant to the deployment site through a cystoscope.

Optionally, the device includes a dedicated optical unit for viewing the progress of an implantation procedure.

Optionally, the implant is delivered to the implantation site by the dilation device. Optionally, the dilation device and the implant are delivered to the implantation site as separate units.

Optionally, the implant release mechanism is operable through the shaft by an attached hand-piece.

According to an aspect of some embodiments of the invention, there is provided a inflatable dilation device.

Optionally, the dilation device is at least one generally cylindrical balloon, or at least two balloons that are generally toroidal or generally semi-ellipsoidal. Optionally, the dilation device is at least one resilient self-expanding member configured for delivery in a compressed condition to a deployment site for the implant.

Optionally, the device includes a compression device for maintaining one or more of the dilation device, the cutter, and an implant in a non-operative condition during delivery to an implantation site. Optionally, the cutter is configured for delivery to the implantation site inside a sheath, and for extension out of the sheath for use. Optionally, the sheath carrying the cutter is located on an outer surface of the dilation device. Optionally, the sheath carrying the cutter is located inside the dilation device, and the dilation device includes a self-sealing area through which the cutter exits to form the cut. Optionally, the sheath carrying the cutter is attached to the dilation device.

Optionally, the dilation device and the sheath carrying the cutter are delivered to the implantation site as separate units.

According to an aspect of some embodiments of the invention, the cutter is configured to form a cut having a T-shaped, or an I-shaped, or an inverted L-shaped cross-section.

According to an aspect of some embodiments of the invention, the cutter and the implant cooperate to form the implant-receiving cut.

Optionally, the elements that form the cutter are substantially linear, or include one or more arcuate segments.

According to an aspect of some embodiments of the invention, the cutter is configured to for a cut by electric power on the inside of a urethra.

Optionally, the cutter includes one or more sharp edges.

Optionally, the cutter is configured to be connected directly to a source of electric power or to a piezoelectric transducer.

Optionally, electric power is provided intermittently to the cutter during operation according to a duty cycle. Optionally, the cutter is configured to deliver electric power to an area of tissue being cut, and portions of the cutter that do not deliver electrical power to the area being cut are electrically isolated from other tissue areas. Optionally, electrical isolation is provided by a coating of a polyxylylene or a fluoropolymer or other material having dielectric properties.

According to an aspect of some embodiments of the invention, there is provided a device for delivering an implant as described, further including a mechanism for closing the implant-receiving cut by application of an adhesive, or by a clamp, or by a suture.

According to an aspect of some embodiments of the invention, there is provided a method of treatment of an intra-body lumen, for example, a constricted portion of a urethra, by inserting an implant formed of a resilient material into a lumen to be treated, expanding the lumen using a dilation device, forming a cut in tissue surrounding the lumen, for example, the prostate at the area to be treated, and deploying the implant in the cut.

Optionally, the implant is delivered to the implantation site in a compressed condition, and is deployed in the cut in at least a partially uncompressed condition.

Optionally, the cut is formed with a T-shaped or an I-shaped or an inverted L-shaped cross-section.

Optionally, the cut is formed by a cutter delivered to the implant site, or by the implant, or by cooperation of a cutter and the implant.

Optionally, the cut is formed by a sharp edge of a cutter and/or the implant, and/or by the action of electrical power delivered to the area being cut.

Optionally, electric power is provided continuously or intermittently during the cutting operation.

Optionally, the cut is performed by a oscillating blade which is connecting to a piezoelectric transducer.

According to an aspect of some embodiments of the invention, the method further includes closing the implant-receiving cut after deployment of the implant.

Optionally, the implant-receiving cut is closed by application of an adhesive, or by a clamp, or by a suture.

Optionally, the implant is configured as a C-shaped open ring, an overlapping spiral ring, or a closed ring, or a helix.

Optionally, the dilation device is a balloon and is expanded by inflation, or is a self-expanding device and is expanded by releasing it from a carrier in which it is delivered to the deployment site.

Optionally, two or more of an implant, the dilation device and a cutter are delivered to the implantation site as a single unit. Optionally, an implant, the dilation device, and a cutter are delivered to the implantation site as separate units.

According to an aspect of some embodiments of the invention, there is provided a method for dilating a constriction of a urethra in which a cut is formed in the prostate surrounding the constriction by an electric or ultrasonic cutter from inside the urethra, and by inserting an implant into the cut.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are described below, by way of example only, with reference to the accompanying drawings. With specific reference now to the drawings in detail, it is to be understood that the particulars shown in the drawings are by way of example and for purposes of illustrative discussion of embodiments of the invention. In this regard, the description taken with the drawings makes apparent to those skilled in the art how embodiments of the invention may be practiced.

In the drawings:

FIGS. 16A-16H are schematic illustrations of delivery configurations for a cutter, illustrated by way of example, as electrically operated, in relation to a dilation device according to some embodiments of the invention;

Throughout the drawings, where convenient, like parts are given the same reference signs.

DETAILED DESCRIPTION OF THE INVENTION

Introduction

Figure 1:
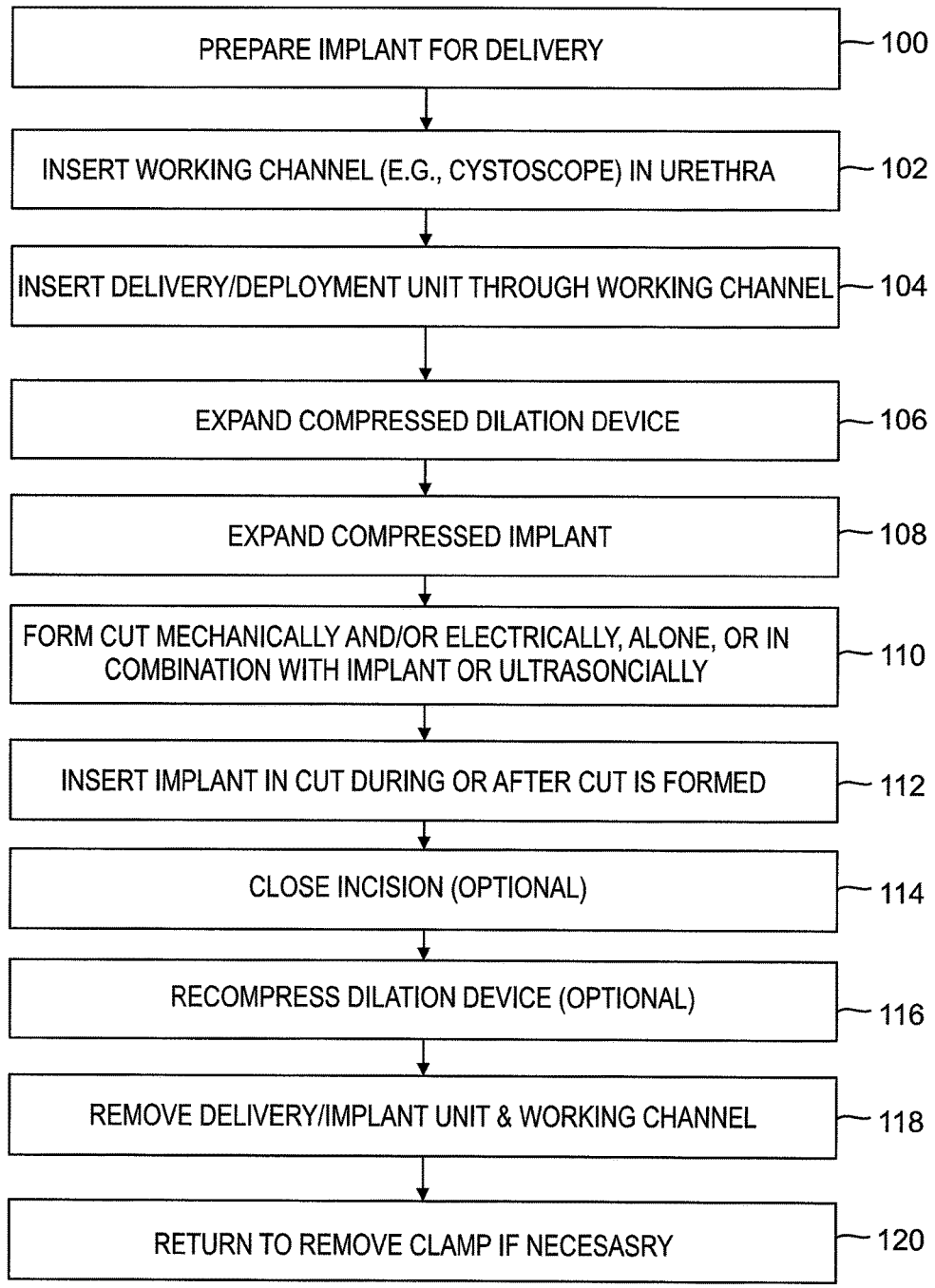
FIG. 1 is a simplified flow diagram illustrating a method of delivering an implant, preparing a cut in which the implant will be deployed, and releasing the implant for deployment according to some embodiments of the invention.

The present invention, in some of its embodiments, relates to devices and methods for treatment of intra-body lumens, and, more particularly, but not exclusively, to devices and methods for dilating and/or assisting in dilation and/or maintaining dilation of the urethra to relieve obstruction resulting, for example, from benign prostatic hyperplasia (BPH).

Various exemplary embodiments of the invention will be described in the context of treatment of BPH. However, it is to be understood that the devices and methods are also applicable to dilation of other constricted bodily lumens, for example, a bile duct in case of pancreatic or other carcinomas, intestine, e.g. colon carcinoma, or blood vessel.

Some embodiments of the invention concern an implant in the form of a resilient member, e.g., a strip or a wire, configured for deployment in a cut formed in an intra-body lumen. Optionally, by way of example, the cut may a narrow slit configured to receive a coiled wire implant, or a groove configured to receive an implant in the form of an arcuate strip. Optionally, the cut is wider at the base than at its opening. Optionally, and again by way of example, the cut may have a U-shaped or a T-shaped cross-sectional configuration.

Optionally the cut is a complete circle, or less than a complete circle. In either case, if the implant is not a complete circle, it may optionally be the same length as, or shorter than the cut when deployed. Optionally, the cut is helical to receive a helical implant.

Optionally, the width of the implant is substantially the same as or less than the width of the base of the cut.

In some embodiments of the invention, the implant is delivered in a compressed e.g., folded or coiled condition, and is restored to at least a partially relaxed uncompressed condition during deployment. If fully relaxed, the elasticity of the implant allows it to maintain its size and shape in the cut, thereby preventing collapse of the lumen in the region of the cut. If the implant is not restored to a completely relaxed condition upon deployment, it applies radially outward force in the cut to enable further post-deployment dilatation.

In some embodiments of the invention, the compressed implant is expanded before the cut is made. Optionally, it is expanded while the cut is being made. Optionally, it is expanded after the cut has been completed. In some embodiments of the invention, for the first two options, the cutter itself may deploy the implant by pulling it along behind itself while the cut is being made. In some embodiments of the invention, for the third option, a separate device may be employed to deploy the implant at the base of the cut. Optionally, the deployment device is a balloon which is inflated to push the implant into the cut.

Optionally, the implant is configured as a C-shaped open ring, or as a spiral (overlapping, closed) ring, or as a closed ring, or as a helix. Optionally, the implant is made of a strip defined by repeated segments. Optionally, the implant is made in the form of a strip having a mesh structure.

In some embodiments of the invention, the implant is configured for delivery to a deployment site through the urethra, for example, using a cystoscope to provide a working channel.

In some embodiments of the invention, the implant is formed of a biocompatible metal. Optionally, the metal is nitinol. Optionally, it is stainless steel. Optionally, it is chromium-cobalt. Optionally, it is formed of a non-metallic biocompatible material, for example, a biodegradable or non-degradable polymer. By way of example, a suitable non-degradable polymer is polyurethane. Suitable biodegradable polymers include polyglycolic acid (PGA) or polylactic acid (PLA).

In some embodiments of the invention, the implant carries a drug which is eluted or otherwise released for delivery after deployment, for example, to relieve hyperplasia.

In some embodiments, the implant is delivered to the deployment site and is implanted by a deployment device that includes an implantation unit, which, in turn, is comprised of a cutter, and a device for dilation of the urethra or other lumen before and while the cut is being made. For simplicity, the pre-dilation device will be referred to as a "dilation device".

One optional configuration for the deployment system according to some embodiments of the invention includes a delivery device comprised of a cutter attached to an implant on one shaft, and a dilation device attached to another shaft. As another option, the deployment system includes the dilation device, the cutter, and the implant on a single shaft. In another option, the deployment system includes three separate devices, one for delivery of a dilation device, one for delivery of an implant and a third delivery device for the cutter.

In the various options, some or all of the parts may optionally be provided as a kit, and may be disposable after use.

Optionally, the implantation unit includes an arrangement configured to releasably hold the implant while it is being delivered and/or deployed. Optionally, the coupling arrangement is attached to the distal end of the cutter. Optionally, the delivery device includes a release mechanism for disconnecting the implant from the coupling arrangement. Optionally, the release mechanism is operable through a shaft which carries the cutter and/or the implant. Optionally, it is operable by a separate releasing device and/or a separate shaft.

In some embodiments of the invention, the dilation device is at least one inflatable balloon, for example, having a generally cylindrical configuration. Optionally, it is at least two inflatable balloons, for example, having a generally toroidal configuration. In some such embodiments, there is also provided a connector configured to be attached to a pressure source for inflating the dilation device.

In some embodiments of the invention, the dilation device is formed of at least one metal ring. Optionally, it is a helical coil. Optionally, it is at least one mesh ring, or at least one ring having a repeating structure. Where more than one dilation device is provided, they may all be located distally relative to the cutter. Alternatively, the cutter may be positioned between two dilation devices.

In some embodiments of the invention, the dilation device is delivered to the implantation site in a compressed condition.

In some embodiments of the invention, the cutter is positioned as a linear extension of the delivery shaft while it is inserted in the lumen. Optionally, it is folded back against the shaft during delivery to the implantation site. In either case, it is opened for operation. By way of example, the cutter is opened approximately 90 degrees relative to the shaft from its delivery position. Optionally, the cutter is rotatable by the shaft to form the deployment cut for receiving the implant.

In some embodiments, the cutter is delivered in a sheath, and is configured to be put in an operative configuration by it out of the sheath, or by withdrawing the sheath. Optionally, the cutter sheath and the dilation device are delivered as a single unit. Optionally, the cutter sheath is delivered attached to the outside of the dilation device. Optionally, the cutter is delivered to the implantation site in a pre-formed channel topologically on the outside of the dilation device.

Optionally, the cutter sheath is delivered inside the dilation device, optionally attached to an inner surface of the dilation device.

In some embodiments, for which the cutter is delivered inside the dilation device, a n air-tight port on the surface of the dilation device allows extension of the cutter for use. Optionally, the cutter is extended through a self-sealing path on the inside and/or the outside surface of the dilation device.

In some embodiments of the invention, the cut for receiving the implant is made purely mechanically, for example, by a sharp blade. In some embodiments, it is made by an ultrasonic cutter. In some embodiments, it is made by a thermal process, for example, by ultrasound, or by electric current. A thermal process may be advantageous in that it may facilitate forming the cut, and may aid in coagulation and sealing, In some embodiments, the cutter operates by a combination of mechanical cutting and electric current. Optionally, in some electrical embodiments, the current may be provided continuously, or intermittently, for example, according to a selectable duty cycle.

According to some embodiments, the implant itself cooperates with a cutter to form the implant receiving cut, either electrically, mechanically, or by a combination of mechanical and electrical action. In some embodiments, the implant alone performs the cut.

Some embodiments of the invention concern a method of treatment of an intra-body lumen, by way of a non-limiting example, a portion of a urethra which is constricted due to BPH. In such embodiments, an implant formed of a resilient material is inserted into the lumen in a compressed i.e., folded or coiled, condition, and is at least partially restored to its relaxed, i.e., uncompressed, condition for deployment in a peripheral cut formed in the tissue surrounding the lumen at the area to be treated, e.g., in the prostate. The implant is inserted in the cut, thereby dilating the lumen in the area of the cut. Optionally, the lumen is dilated by a separate dilation device before and while the cut is being made.

In some method embodiments, the implants, a delivery device including an implantation unit, are configured according to at least some of the embodiments described above.

In some embodiments of the invention, one implant is deployed to dilate a local obstruction. Optionally, multiple implants are deployed for extended obstructions.

In some method embodiments in which the implant is attached to the cutter for delivery to the deployment site, the implant is deployed by the cutter itself as the cut is being formed. Optionally, it is released from the cutter and deployed after the cut has been formed. In that case, and if the implant is delivered separately from the cutter, it is deployed by a separate device that pushes it into the cut.

In some embodiments, the incision through which the implant is deployed is closed after implantation to promote healing. Optionally, this can be done by use of an adhesive, for example, delivered by the implant itself, by one or more clamps or by suturing.

Before explaining at least some embodiments of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

General Description of Method of Deployment:

Referring first to FIG. 1, the general principles of deployment of implants according to some embodiments of the invention are shown in flow chart form. This general discussion may assist in the understanding of the construction of the implants, and the various features of implant delivery devices according to some embodiments.

At 100, an implant is prepared for use by configuring it in a manner that avoids damage to tissue during delivery to a desired location for implantation, and by releasably attaching the implant to a delivery device.

At 102, a working channel, provided, for example, by a conventional cystoscope, is inserted through the urethra. At 104, the deployment system (in one of the configurations described below) is inserted through the working channel to the desired location.

At 106, a dilation device, which has been delivered in a compressed condition, is expanded to enlarge the urethra at the implantation site. At 108, the implant, which has been delivered in a compressed state, is also expanded. At 110, a cut is made in the tissue of the prostate. This may be done mechanically, or thermally, for example, ultrasonically, or by electric current. At 112, the implant is deployed in the cut. The implant may be deployed while the cut is being made or after the cut is completed, and may cooperate with the cutter in forming the cut.

At 114, if it is desired to augment natural re-growth of tissue around the incision, it may optionally be closed. This may be done by an adhesive, a removable clamp, or a suture Optionally at 116, the dilation device is recompressed. At 118, the delivery system and the working channel are withdrawn.

At 120, if a clamp is used at 114 to close the incision, it is later removed.

Note that depending on the length of the obstruction, it may be necessary to deploy more than one implant along the prostatic urethra. In that case, the delivery device is prepared with the required number of implants at 100. Then at 110, the required number of cuts is made, optionally simultaneously and at 112, the implants are inserted in the cuts, again, optionally, simultaneously. For multiple implants, it may be desirable to anchor the delivery device in the bladder after 108.

Figure 2H:
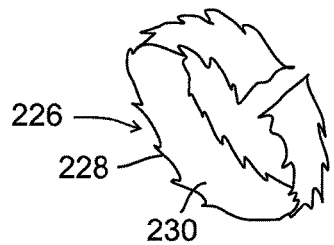
FIGS. 2A-2N and 2P-2R illustrate exemplary configurations of implants according to some embodiments of the invention.
Figure 2I:
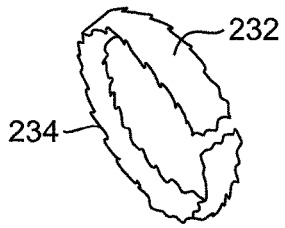
Figure 2J:
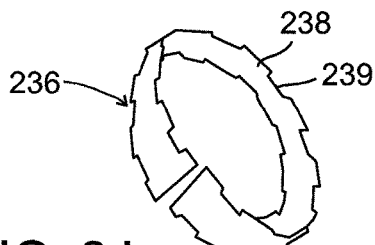
Figure 2K:
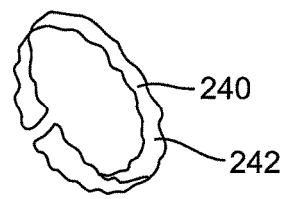

Exemplary Implant Configurations:

Turning now to FIGS. 2A-2N and 2P-2R, there are shown several exemplary, but non-limiting embodiments of implants according to the invention. FIGS. 2A-2C are end views that respectively illustrate a flat, generally C-shaped implant 200, a flat overlapping (i.e., spiral-shaped) implant 202, and a flat generally circular closed-ring implant 204. FIGS. 2D-2G are perspective views illustrating substantially circular but open-ended ring implants. FIG. 2D illustrates an implant 206 in the form of a flat open-ended solid strip, FIG. 2E illustrates an implant 208 in the form of a flat open-ended strip defined by repeated open segments, and FIG. 2F illustrates an implant 210 in the form of a flat open-ended mesh.

FIGS. 2A and 2D show essentially the same implant structure except that implant 206 (FIG. 2D) is longer, and, is therefore more nearly a closed circle. The implants shown in FIGS. 2E and 2F may alternatively be shorter, and therefore more open as in FIG. 2A.

In the embodiments illustrated in FIGS. 2A and 2D-2F, implants 200 and 206-210 include respective pointed leading ends 214, 216, and 218.

FIG. 2G illustrates an alternative construction of an implant in which the ends 222 and 224 are slightly curved. Optionally, in an un-illustrated variation, the ends may be substantially straight. As will be appreciated, any of the strip implant embodiments described herein may have curved or straight leading ends Pointed leading ends may be advantageous to assist in forming I-shaped cuts as described below and to facilitate entry into a cut formed in the prostate to receive the implant, also as described below. Curved leading edges may also help facilitate entry into the receiving cut.

Implant 220 also illustrates a variation of the embodiments of FIGS. 2A and 2D in which the length of the strip is greater than that of implant 200 but less than that of implant 206. The result is a substantially C-shaped configuration.

Other strip implant embodiments having generally non-linear longitudinal edges are shown in FIGS. 2H-2K. Implant 226 (FIG. 2H) includes saw tooth 228 on its edges 230. Implant 232 (FIG. 2I) includes barbs 234. Implant 236

(FIG. 2J) includes repeated straight segments 238 and 239. Implant 240 (FIG. 2K) includes wavy edges 242.

Figures 2L, 2M:
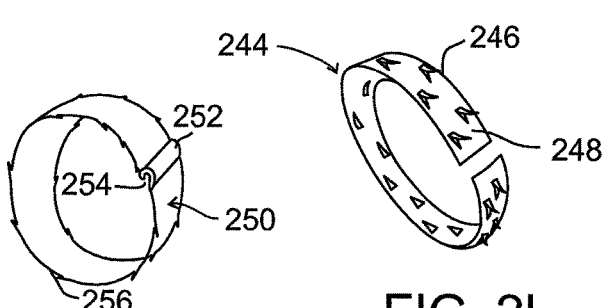

Two other exemplary flat-strip variations are shown in FIGS. 2L and 2M. Strip 244 (FIG. 2L) incorporates barbs 246 on its flat surface 248, and implant 250 (FIG. 2M) includes barbs 256 on its longitudinal edges. The surface and edge configurations of the embodiments of FIGS. 2L and 2M may be helpful in anchoring the implants in the tissue.

Implant 250 (FIG. 2M) is a fully closed ring with hooks 252 and 254 on its ends that engage with each other. The longitudinal edges 256 are shown barbed, but any of the other edge embodiments discussed above may be substituted. In this embodiment, the implant is delivered to the implantation site rolled up as illustrated in FIG. 2R, and the hooks are engaged before implantation. The rolled up configuration is more easily delivered, while engaging hooks 252 and 254 to close ring 250 may facilitate a stronger structure with a controlled expanding diameter.

Figure 2N:
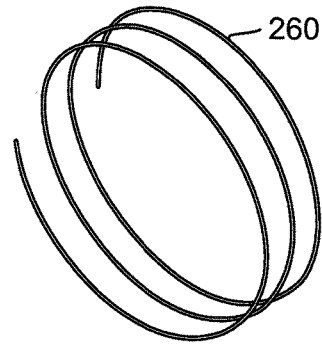
Figure 2R:
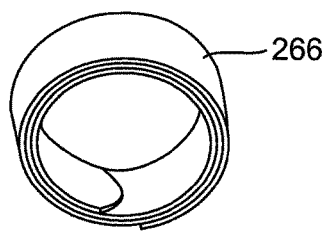
Figure 2Q:
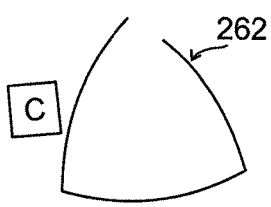
Figure 2P:
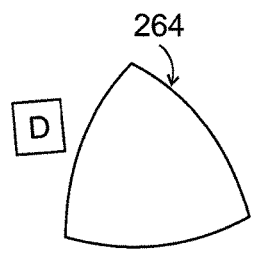

As a further alternative, an implant may be in the form of a resilient helical wire 260, as illustrated in FIG. 2N. Such an embodiment, formed, example, of multiple turns of resilient wire to provide the required width and strength may be occupy less space permitting use with small diameter cystoscopes as the working channels, while strip implants may be useful if a greater radial force needs to be applied to the lumen.

The width of the strip implants shown in FIGS. 2A-2M may be in the range of about 0.1 mm to about 10 mm wide and in the range of about 0.05 mm to about 0.5 mm thick. Wire implants (FIG. 2N) may range in width from about 0.1 mm up to about 10 mm and may be formed a wire having a diameter of 0.01 mm or more.

The embodiments described above are generally circular or arcuate. Other shapes are also possible. Additional non-limiting examples include open or closed generally triangular configurations as shown at 262 and 264 in FIGS. 2P and 2Q, respectively. The triangular outline may be advantageous in that it matches the cross-section of the unobstructed urethra. Matching the cross-section of the urethra may be desirable since it may reduce forces on the tissue by the implant, and may improve the efficiency of handling the tissue forces.

The implants illustrated in FIGS. 2A-2N and 2P-2Q may be formed of any biocompatible metals, biodegradable or non-degradable polymers suitable for the purpose. By way of non-limiting examples, metals may include nitinol, stainless steel, or chromium-cobalt. An exemplary non-degradable polymer is polyurethane. Exemplary biodegradable polymers are polyglycolic acid (PGA) or polylactic acid (PLA).

The implants described are formed of a resilient, i.e., elastic, material to permit delivery in a compressed configuration, and re-expansion upon deployment. For example, a strip implant may be delivered in a rolled up condition, as illustrated in FIG. 2R at 266.

FIG. 2G shows a hole 270 at the leading end of the implant (also shown in FIG. 2R). This configuration accommodates a dedicated pin/hook which is part of release mechanism that is inserted though that hole, as described below.

Optionally, the cuts are configured to match the configuration of the implant. Thus, for the implants illustrated in FIGS. 2A-2M, the cut may be a U-shaped or T-shaped. It should be noted that the wire embodiment 260 of FIG. 2N is optionally intended to be inserted in a groove like that for the strip embodiments, and thus the turns will be substantially compressed longitudinally after implantation.

For the strip embodiments of FIGS. 2A-2M, it may be advantageous for the groove to be wider at the base than at its opening and for the implant to be substantially the same width as the base of the groove. This may help anchor the implant in the tissue since the cut closes around the deployed implant due to tissue re-growth and resilience.

In some embodiments of the invention, the implant is coated with, or includes pores through which a drug is eluted after deployment to relieve hyperplasia or for any other desired purpose. Alternatively, a separate band configured for delivery of drug material may be implanted. As previously noted, the implant is advantageously delivered in a compressed state, and is restored to at least a partially relaxed condition upon deployment. If the implant is restored to its fully relaxed condition, it maintains its size and shape in the cut, thereby preventing re-collapse of the lumen in the region of the cut. If the implant is not completely relaxed upon deployment, it applies radially outward force in the cut to enable further post-deployment dilatation.

Figure 3:
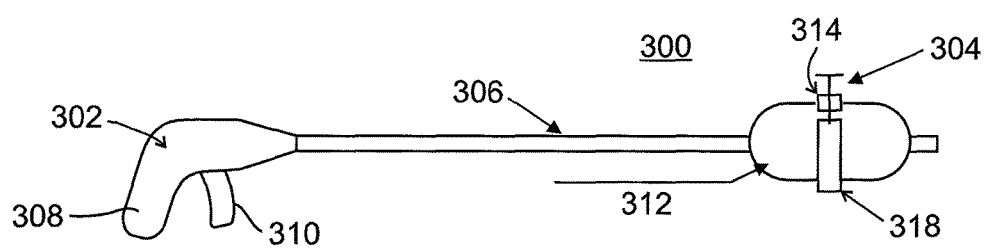
FIG. 3 is a schematic perspective illustration of an exemplary delivery device including a deployment unit.

The resiliency of the implant is chosen mainly to facilitate deployment in a much smaller profile than its open/final condition Exemplary Delivery System Embodiments:

A device according to some embodiments of the invention is illustrated schematically at 300 in FIG. 3. Generally stated, device 300 is comprised of a hand-piece 302, an delivery system/unit 304, and a connecting arm or shaft 306. Hand-piece 302 includes a hand grip 308 and an operating arrangement illustrated for simplicity as trigger mechanism 310.

It should be understood that these components are illustrated by way of example, and that other configurations, and other optional features may be included.

In an actual implementation, hand-piece 302 may be configured to include some or all the controls and other components necessary for the surgeon to perform the required steps of the surgical procedure. These optionally include one or more of a built-in optical imaging arrangement for positioning the implantation unit at the desired location in the urethra, a coupling for connection to a pressure source for expanding the dilation device as described below, and a mechanism for controlling delivery of the inflation pressure, a mechanism for erecting and rotating the cutter to perform the implant-receiving cut, and an arrangement to release the implant at a desired location and to insert it into the implant into the cut if it is not self-deploying, as well as any other optional manipulations as described herein.

Instead of controls built into hand-piece 302, some of the required functions can be provided by operating wires or rods inserted through shaft 306 (internally or externally to the shaft 306). Optionally, the control wires may optionally be delivered separate from shaft 306 directly through the cystoscope that provides a working channel in a conventional manner. Optical imaging may also be provided by the cystoscope in a conventional manner. Similarly, inflation pressure for the dilation device may be provided by couplers on the cystoscope.

Figure 5L:
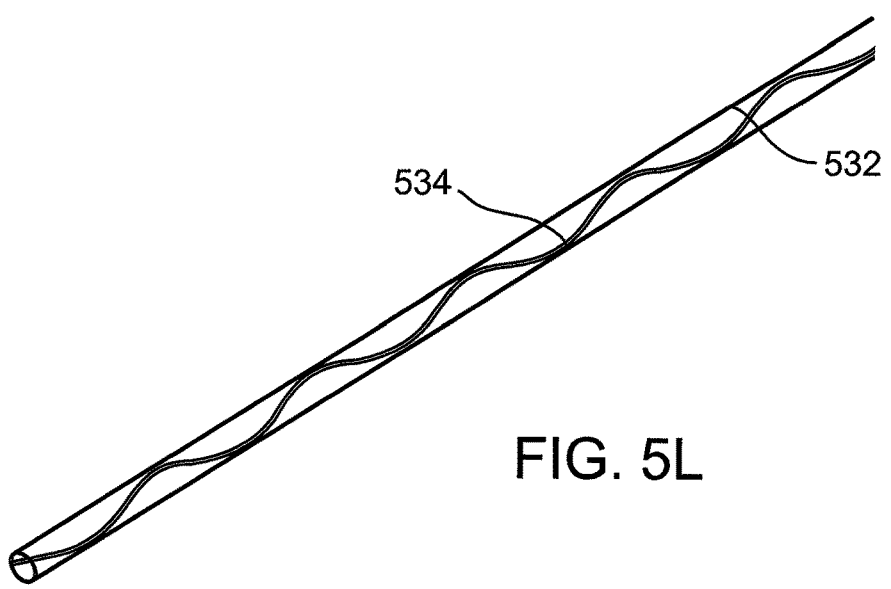
Figure 6A:
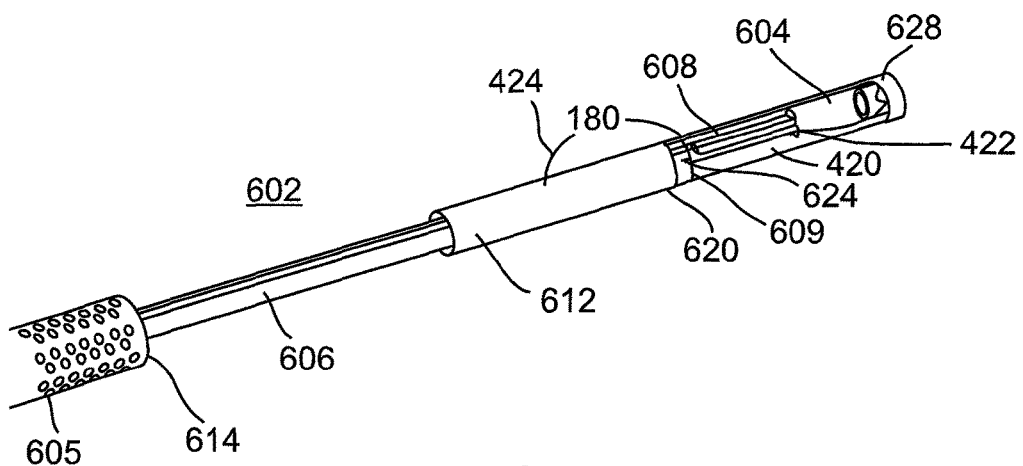
FIG. 6A is an enlarged perspective view of a delivery device with parts removed to show internal features.
Figure 6B:
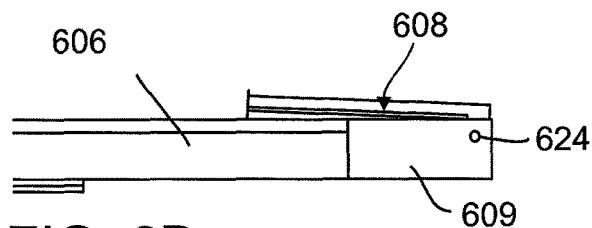
FIG. 6B is a side view of a part of FIG. 6A showing a cutter in a delivery configuration according to some embodiments of the invention.
Figure 6C:
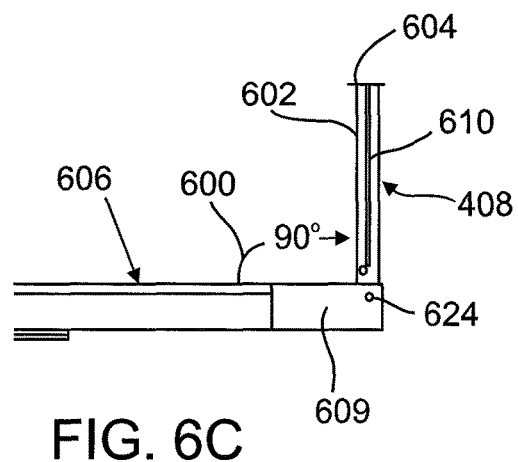
FIG. 6C is a side view showing the cutter of FIG. 6B in its operating configuration showing a cutter in an operating configuration according to some embodiments of the invention
Figure 7:
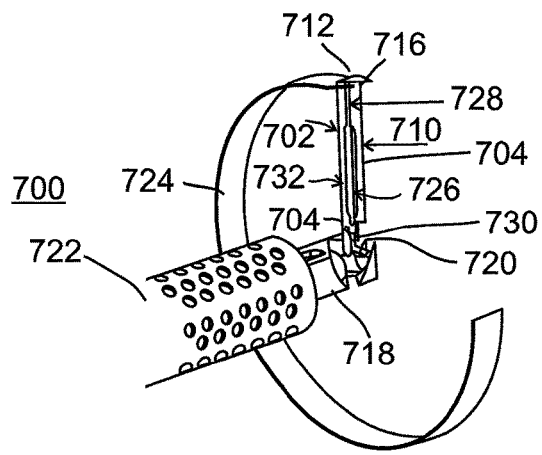
FIG. 7 is a close-up in detail showing a cutter having a T-shaped blade with an attached implant according to some embodiments of the invention.

In the illustrated embodiment, delivery system/unit 304 is comprised of an expandable urethral dilation device 312, shown for purposes of clarity in its (deployed) fully expanded state, a cutting mechanism 314 also shown in a fully deployed state, and a release mechanism (shown FIG. 7 for an implant 318). Optionally, a sheath, examples of which shown at 532 and 612 in FIGS. 5L and 6, respectively), surrounds at least the dilation device 312 and implant 318 before deployment to maintain dilation device 312 and implant 318 in their compressed condition during delivery, and which is opened to allow the dilation device and the implant to be released. Optionally, sheath 612 also surrounds the cutter 314 during deployment.

Further details concerning the construction and operation of exemplary operating controls used by the surgeon during the procedure to open and control the cutter, to perform the cut and to release and deploy the implant into the prostate, along with exemplary embodiments of dilation devices and cutting mechanisms are described below.

Figure 4:
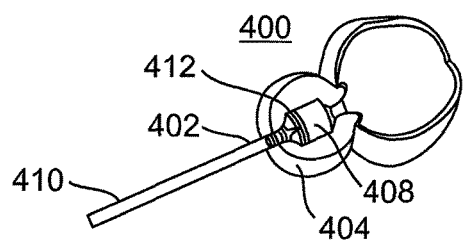
FIG. 4 illustrates part of the delivery device of FIG. 3 inserted in a urethra constricted by an enlarged prostate in preparation for formation of a cut and deployment of an implant.

FIG. 4 is a schematic illustration of a delivery system/unit 400 forming part of a device such as 300 shown in FIG. 3. Delivery system/unit 400 is shown deployed in a urethra 402 surrounded by an enlarged prostate gland 404. To facilitate deployment, a working channel may be provided by a standard cystoscope (410) including couplers for a light cable, and for an optical system, a fluid inlet, and a fluid outlet, (not shown) through which the connecting shaft 306 (see FIG. 3) is inserted.

Figure 5A:
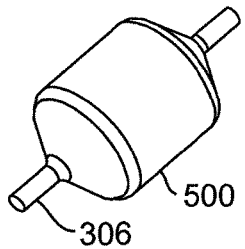
FIGS. 5A-5L are enlarged perspective views of various dilation device configurations according to some embodiments of the invention.
Figure 5B:
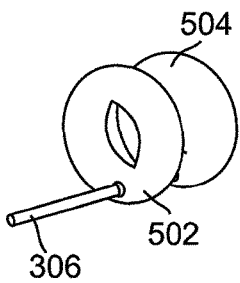
Figure 5C:
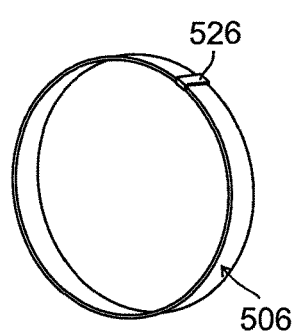
Figure 5D:
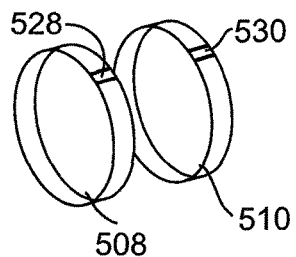

A dilation device 408 is shown in its expanded condition in preparation for performing the cut in prostate 404 and insertion of an implant 412 into the prostate. Further details are omitted in this figure in the interest of clarity, FIGS. 5A-5L show several exemplary embodiments for the dilation device. FIG. 5A shows an inflatable balloon 500, for example, having a generally cylindrical configuration. FIG. 5B shows an arrangement of two generally toroidal inflatable balloons 502 and 504. Such inflatable embodiments are coupled to a pressure source, for example, through a tube (not shown) in shaft 306 (FIG. 3).

Other double-balloon configurations are also possible, for example, half-ellipsoids arranged in tandem.

In some embodiments of the invention, the dilation device is formed of one or more metal rings. A one-ring embodiment is shown at 506 in FIG. 5C. A two-ring embodiment including rings 508 and 510 is shown in FIG. 5D). Alternatively, the dilation device may be a helical coil 512 (see FIG. 5E). Further alternatives include a mesh ring 514 or two mesh rings 516 and 518 (FIG. 5F or 5G), or one repeated-segment ring 520 or two such rings 522 and 524 as shown in FIGS. 5H and 5I). Further alternatives include a coiled strip 526 or two coiled strips 528 and 530 (FIGS. 5J and 5K). The single-element embodiments of FIGS. 5A, 5C, 5F, 5H and 5J may be positioned proximally or distally of cutter 314 (FIG. 3). The double-element arrangements of FIGS. 5B, 5D, 5G, 5I and 5k may be positioned with one proximally and the other distally located relative to the cutter. As a further alternative, the cutter may be delivered attached on the outside of the dilation device, or inside the dilation device, as discussed below.

In some embodiments of the invention, the dilation device is delivered to the implantation site in a compressed condition, for example, rolled up or radially compressed. For the balloon dilation devices shown in FIGS. 5A and 5B, and for the embodiments shown in FIGS. 5C, 5D, and 5F-5I, this is achieved simply by folding. FIGS. 5J and 5K show, by way of example, a rolled ring strip 526, and two folded rings 528 and 530 compressed in the form of a roll.

Figure 5E:
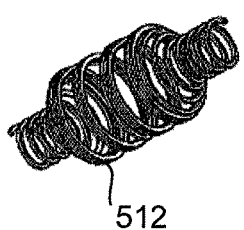
Figure 5F:
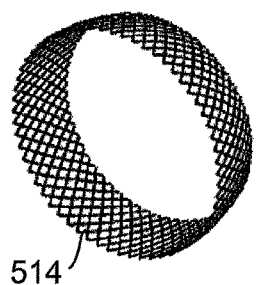
Figure 5G:
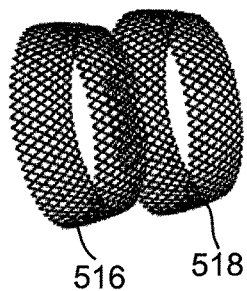
Figure 5H:
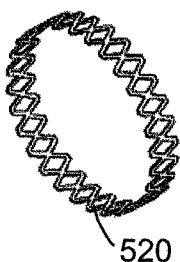
Figure 5I:
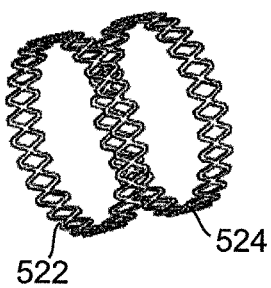
Figure 5J:
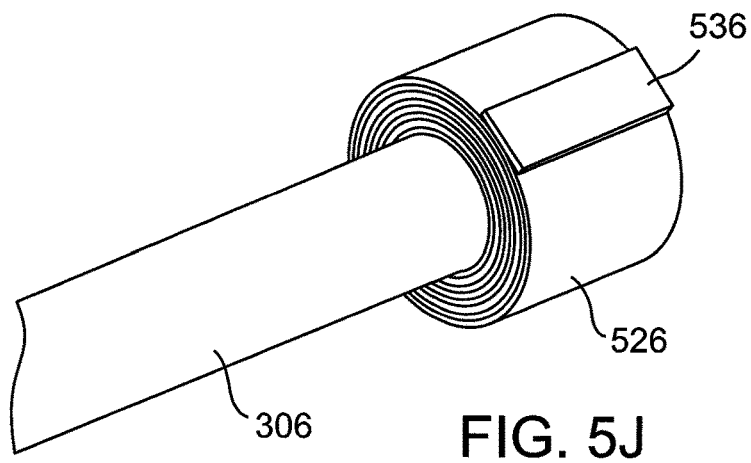
Figure 5K:
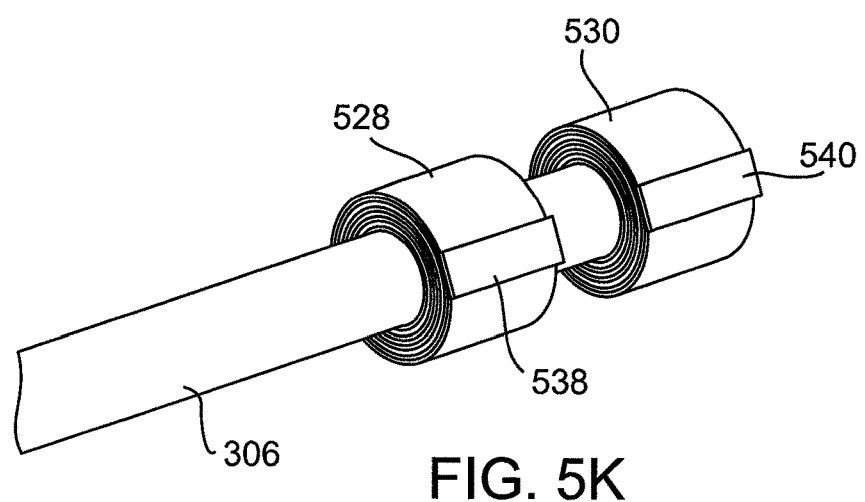

The folded dilation devices of FIGS. 5A-5K are optionally held in compressed condition by a cover, for example, a surrounding sheath 532, as illustrated for a spiral dilation device 534 (FIG. 5L) or 512 in FIG. 5E. In the case of rolled strips 526-530, the respective ends 536-540 of the strips overlap.

In some embodiments of the invention, the dilation device is recompressed for removal after the implant has been deployed. For balloon implants, this can be done by releasing the pressure, or by application of negative pressure. Resilient dilation devices as in FIGS. 5C-5K may be recompressed by re-enclosure in the delivery sheath. Optionally, in some instances, since the prostate has already been dilated by the implant, the dilation device can be withdrawn without recompression. In that case, it is compressed as necessary as it passes through the working channel.

Balloons 500-504 may be formed of any suitable material conventionally used for dilating intra-body lumens. The alternative embodiments illustrated in FIGS. 5C-5I may be formed of an elastic biocompatible metal, for example, nitinol, stainless steel, or chromium-cobalt. Optionally, they may be formed of a biocompatible resilient polymer such as polyurethane. Optionally they may be formed of biodegradable resilient polymers such as Polyglycolic acid (PGA) or Polylactic acid (PLA).

The dilation devices illustrated in FIGS. 5A-5L are sized according to the lumen being treated. For the prostate implants described and shown herein, the devices may have expanded diameters in the range of 1 mm-100 mm and widths in the range of 1 mm-70 mm. Helical coil 512 of FIG. 5E may have a diameter in the range of 1 mm-100 mm and an expanded length of 5 mm-100 mm. A balloon dilation device is preferably formed of a non-compliant material. An expansion pressure in the range of about 0.1 ATM to about 20 ATM, or greater of lesser values may be employed.

FIG. 6A illustrates schematically 600 several features of an exemplary delivery system/unit 602 according to some embodiments of the invention. Delivery system/unit 602 includes a cutter mechanism attached at distal end of shaft 606 which extends through working channel 604 provided by cystoscope 605, and is connected to hand-piece 302 as shown in FIG. 3.

A delivery system/unit 602 according to some embodiments includes a cutter 608, and carries a dilation device and the implant, shown and described above, but omitted in FIG. 6A for clarity. For deployment, cutter 608 is pivotally attached to a hinge mechanism 609 or is moveably mounted in any other suitable way. Other embodiments are illustrated in FIGS. 14-17 and described below.

FIG. 6A also shows a generally tubular sheath 612 which optionally surrounds the entire length of delivery system/unit 602. The distal part of sheath 612 is cut away between a point 610 in FIG. 6A and its distal end 618 to show internal details. Sheath 612 covers the dilation device, and implant 504, and, optionally, cutter 608, to maintain these parts in a compressed condition during delivery.

In FIG. 6A, cutter 608 is shown in a delivery orientation in which it extends distally. FIG. 6B illustrates an alternative exemplary delivery orientation in which cutter 608 is folded back i.e., in the proximal direction, against shaft 606.

For both of the embodiments of FIGS. 6A and 6B, cutter 608 is pivoted to an open position for use on a hinge pin 624. FIG. 6C shows cutter 608 in an operative position, at a suitable angle relative to shaft 606, for example, approximately 90 degrees. As described below, in this, and some other configurations, cutter 608 is rotated by shaft 606 to form the cut for receiving the implant. Exemplary cutter deployment mechanisms and exemplary cutter operating modes (for example, purely mechanical or thermally by ultrasound or electrical current, or by a combination of mechanical and electrical operation) are described below.

FIG. 7 illustrates an exemplary delivery system/unit 700 including a cutting element 702 that forms a T-shaped cut according to some embodiments of the invention. As shown, cutter 702 is comprised of a stem 704 including a sharp leading edge 710 which forms the stem of a T-shaped cut, and a crosspiece blade portion 712 that includes a pointed end 716. Cutter stem 704 is pivotally connected to a delivery device shaft 718 by a pivot mechanism 720. Shaft 718 extends through the working channel 722 to the operating hand-piece, and is rotatable to perform a peripheral cut into the prostate. Shaft 718 may be manually rotatable, or may optionally be rotated by a low-speed motor located in the hand-piece. In some embodiments described below in which the cutter is attached to the dilation device, it is rotated by the dilation device.

When the cutter is rotated by shaft 718, blade portion 712, cuts into the prostate wall (which has been stretched by the dilation device), thereby forming the base of a cut having a T-shaped cross section. The leading edge 710 of blade stem 704 forms the stem of the T-shaped cut.

Still referring to FIG. 7, in the illustrated embodiment, cutter 702 may be encased in the same sheath (not shown) as the implant and the dilation device, and may be attached to pivot mechanism 720 by a spring mechanism (not shown) so it is self-opening when the sheath is withdrawn. A pull-wire extending through shaft 718 (also not shown) or any other suitable arrangement may alternatively or additionally be provided to erect and/or retract cutter 702 after use. FIGS. 6A-6C illustrate delivery and operational positions for cutter 702. Other delivery and operational positions are described below.

FIG. 7 illustrates an embodiment in which implant 724 is attached to cutter 702 for delivery. In this embodiment, a coupling and release mechanism 726 is built into the cutter. Coupling and release mechanism 726 includes a coupling pin 728 configured to be received in a pin hole (as shown, for example, at 270 in FIG. 2G). A spring 732 holds pin 728 in place. during delivery, cutting, and implantation. A trigger wire 730, optionally extending through delivery device shaft 718, or through the cystoscope working channel 722, and through the coils of spring 732, is connected to withdraw release pin 728. Alternatively, a releasing device separate from the delivery device (not shown) may be provided.

In some embodiments, the cutter carries the implant for delivery. Optionally, in such embodiments, the cutter actually inserts the implant into the cut while it is being made. In other embodiments, the cut is completed before the implant is released.

In some embodiments, the implant is carried separately from the cutter, for example, on a separate shaft or by the dilation device. Further details are presented below.

Figure 8A:
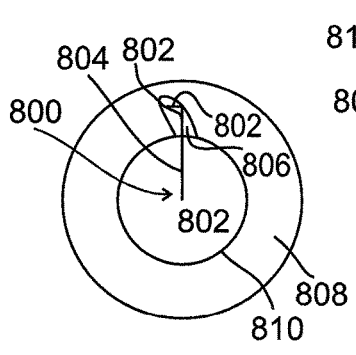
FIG. 8A shows an end view of the initiation of A T-shaped cut according to some embodiments of the invention.
Figure 8B:
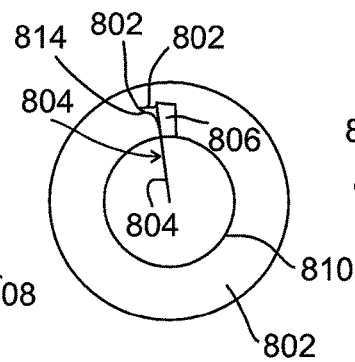
FIG. 8B is a cross-sectional view of a T-shaped cut in process according to some embodiments of the invention.
Figure 8C:
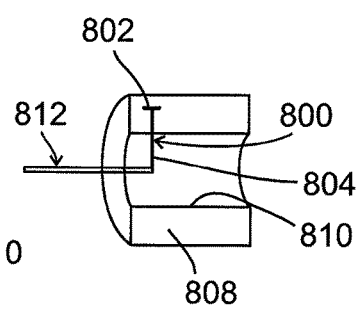
FIG. 8C is a cross-sectional view of FIG. 8B.

FIGS. 8A-8C illustrate the formation of a T-shaped cut. FIG. 8A shows an end view of a cutter 800 including a blade 802 at the initiation of a cut 806 in a prostate 808. FIG. 8B is an end view of a cut in progress. FIG. 8C is a cross-sectional view of FIG. 8B.

As seen in FIGS. 8A-8C, stem 804 of cutter 800 is longer in its extended operational configuration than the radius of the lumen 810, e.g., the urethra, at the cutting site. Therefore prostate 808, which is elastic, pushes radially against the pointed end 812 of blade 802, which facilitates entry of a point (not shown in FIGS. 8A-8C, but corresponding to point 716 in FIG. 7), into the prostate wall and initiation of the cut (FIG. 8A).

In FIG. 8B, the cut is in progress, with cutter 800 being rotated in the plane of the drawing on shaft 812 (see FIG. 8C). As will be understood from FIG. 8C, cutter blade 802 forms the base of a circumferential cut having a T-shaped cross-section, and stem 804 forms the stem of the cut.

The T-shaped cross-section of the implant receiving cut is often desirable as it allows convenient insertion of the implant. Also, the stem of the cut forms tissue flaps on both sides of the cut, which improves the wound healing process. For narrow implants, for example, having a width in the range of between about 0.1 mm and about 2 mm, an I-shaped incision may be employed as described below.

Figure 9A:
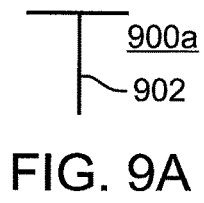
FIGS. 9A through 9G illustrate exemplary cutter configurations according to some embodiments of the invention.
Figure 9B:
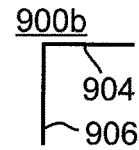

However, other alternatives for both thermally and mechanically performed cuts are possible. FIGS. 9A-9G illustrate some exemplary cutter cross-sections. FIG. 9A illustrates a cutter 900a having a T-shaped blade 902 as described above. FIG. 9B illustrates a cutter 900b having an inverted L-shaped blade formed by a first longitudinal leg 904 and a second radial leg 906. In this embodiment, the implant is inserted through the cut formed by radial leg 906 into the cut formed by longitudinal leg 904.

Figure 9C:
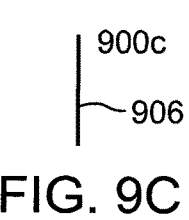
Figure 9D:
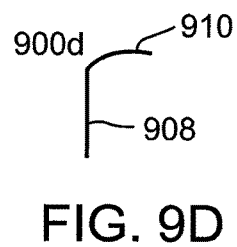

FIG. 9D illustrates a variation of an inverted L-shaped cutter 900d that has a single curved leg having a radial portion 908 and a longitudinal portion 910. As in the case of cutter 900b, the implant is inserted through the cut formed by radial portion 908 into the cut formed by longitudinal portion 910. Cuts formed by blades 900b and 900d may be advantageous in that includes a flap that may improves the wound healing process.

Cutter 900d may further be advantageous as it may be easier to implement and manufacture as a flexible structure that may more easily be inserted and withdrawn due to the absence of a sharp bend between the legs.

FIG. 9C illustrates an I-shaped cutter 900c. For the resulting cut, the implant rests in the base of the cut, i.e. at its radially outer end in the prostate. Advantages of this may include the possibility to form a narrower incision which may enable faster/better recovery of the tissue. It can also be used to accommodate narrow implants.

Figure 9E:
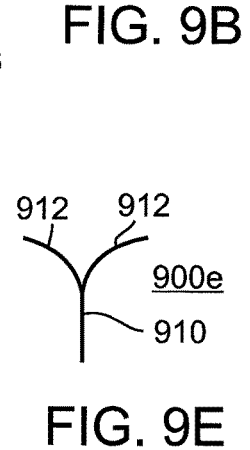

FIG. 9E shows a variation of a T-shaped cutter 900e having a stem 910 and curved branches 912. Like cutter 900d (FIG. 9D), a possible advantage of this embodiment may be easier implementation and manufacture, with a flexible structure that can more easily be inserted in and withdrawn from the tissue of the prostate due to the absence of a sharp corner.

Figure 9F:
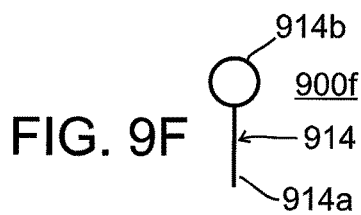
Figure 9G:
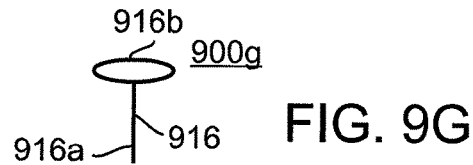

FIG. 9F illustrates a cutter 900f that includes a stem 914a and a round head 914b. Cutter 900g (FIG. 9G) has a stem 916a, but the head portion 916b is generally elliptical. These embodiments may be used to perform T shaped cuts having a smoother, more flexible structure that may facilitate withdrawing the cutter after use because of the absence of sharp edges.

Figure 10:
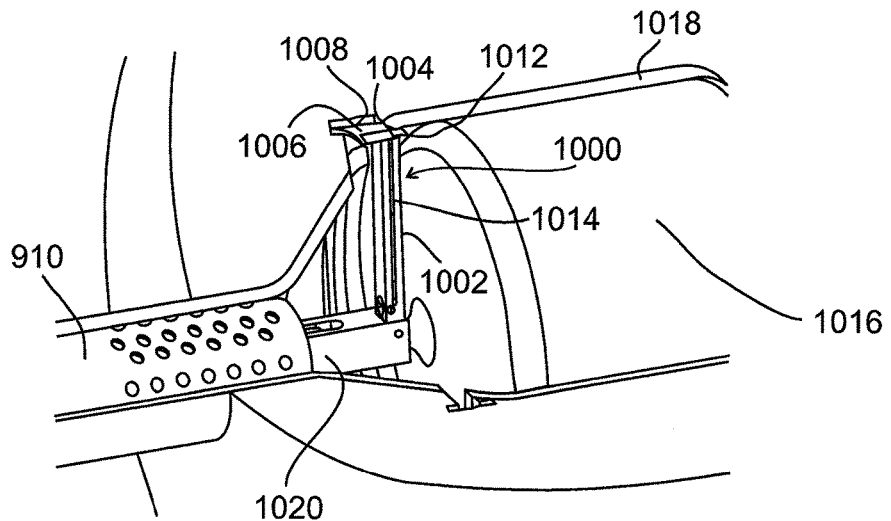
FIG. 10 is perspective view showing an exemplary implantation unit and a partially completed cut for an implant in the form of a non-overlapping open ring according to some embodiments of the invention.

FIG. 10 shows an embodiment in which a cutter pulls an implant into an incision in the prostate during the cutting process. As illustrated, a T-shaped cutter 1000 is having a cross-section as in FIG. 9A, includes a radial stem portion 1002, and a cross-blade portion 1004. The cutting direction is out of the plane of the figure; a sharp leading edge 1012 on cross-blade portion 1004 forms a circumferential portion of the cut 1008 in which implant 1006 is received and a radial edge 1014 of stem 1002 forms a stem of the cut through which implant 1006 is inserted. To permit cutter 1000 to pull implant 1006 into cut 1008 as it is being formed, implant 1006 is attached to the radially inner (back) side of cutter cross-blade 1004 during delivery, cutting and implantation. Attachment may be by means of a coupling/release mechanism, for example, as shown at 723 in FIG. 7, or in any other suitable manner.

To illustrate the cutting operation, the uncut portion of prostate 1010 is not shown in FIG. 10. Implant 1006 is shown already received in the partially formed cut. FIG. 10 also shows dilation device 1016 in its expanded condition within urethra 1018, delivery device shaft 1020.

Figure 11:
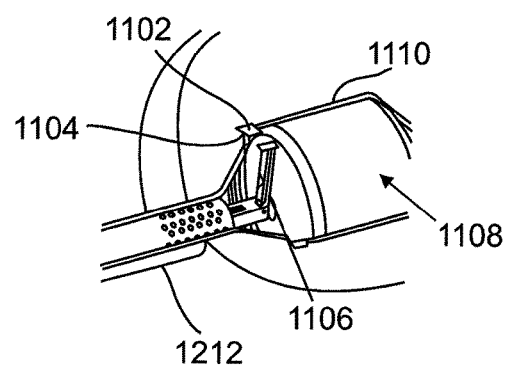
FIG. 11 illustrates a later stage of the cut and implantation shown in FIG. 10.

FIG. 11 shows the completed stage of the cut for an implantation illustrated in FIG. 10. Here, an implant is fully deployed, with its trailing edge 1102 just visible in cut 1104, and already released from cutter 1106, but with dilation device 1108 still inflated and in place in urethra 1110.

Figure 12:
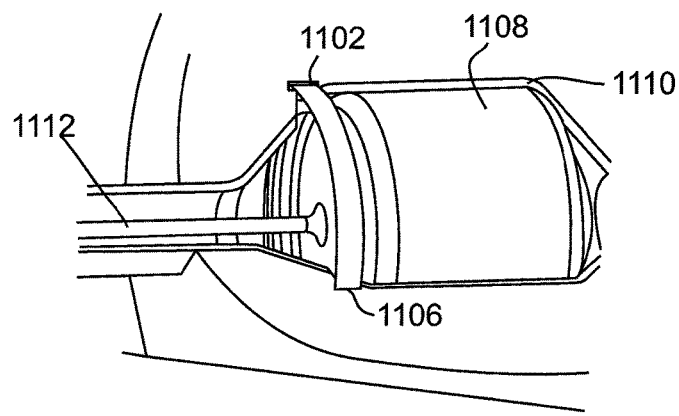
FIG. 12 illustrates the final stage of the cut and implantation shown in FIGS. 10 and 11.

FIG. 12 represents a further stage of the implantation process, with the cutter already withdrawn, but before deflation and removal of dilation balloon 1108. It should be understood that the embodiment of FIGS. 10-12 is one in which the cutter and the dilation device are separate units. Alternatively, as will be understood from the description herein, the cutter and the dilation device may be configured as one unit. In that case both would be withdrawn together.

Figure 13:
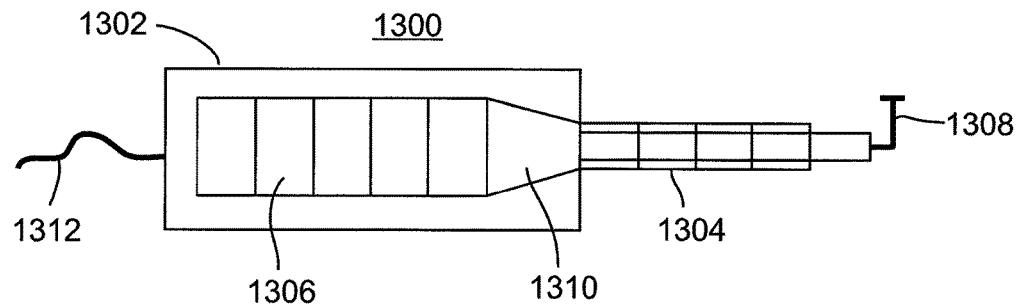
FIG. 13 is a schematic illustration of an ultrasonic cutting system.

Other cutting implementation embodiments will now be described. For example, in addition to direct mechanical action using a sharp blade, the cutter may operate ultrasonically, for example, using a piezoelectric transducer as a driver for the cutter. FIG. 13 shows, in schematic form, an exemplary arrangement for such an embodiment.

Here, system 1300 comprises a hand-piece 1302 within which is located a piezoelectric transducer 1306 which is connected through a coupling horn 1310 and a probe 1304 to a cutter 1308, shown, by way of example as having a T-shaped cross-section.

Hand-piece 1302 is configured to be held by the surgeon during the cutting procedure, and may optionally be located in hand-piece 302 described in connection with FIG. 3. Optionally, hand-piece 1302 can be a separate unit. Electrical power is provided for operating transducer 1306 through a cable 1312 (1312 is missing in FIG. 13), The operation and coupling of transducer 1306 to cutter 1308 is conventional. By way of example, ultrasonic cutters operating in a frequency range of about 20-60 KHz and a power levels in the range of about 5-25 w, or greater or lesser values may be used.

Figure 14:
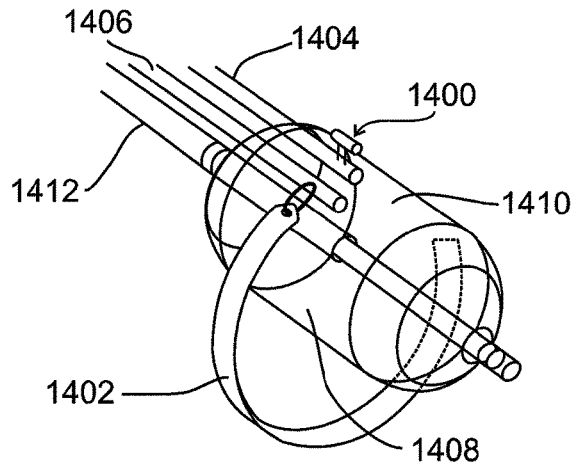
FIG. 14 is a perspective view of a portion of a delivery/deployment unit for an electrically operated cutter, according to some embodiments of the invention, in which an implant, a cutter and a dilation device are delivered to the implantation site by separate shafts.
Figure 15:
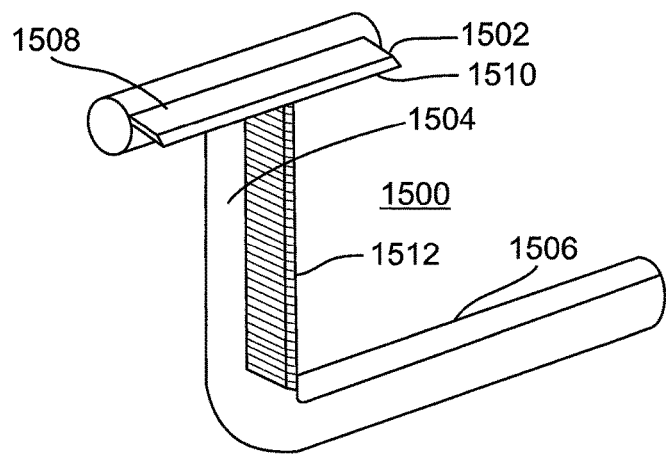
FIG. 15 is an enlarged perspective view showing features of the cutter of FIG. 14 according to some embodiments of the invention.

FIG. 14 illustrates in schematic form, an embodiment in which a cutter 1400 and an implant 1402 are delivered on separate shafts 1404 and 1406 disposed on the outside of a dilation device 1408. FIG. 15 is an enlarged view showing exemplary details of cutter 1400. For purposes of illustration, cutter 1400 will be described as electrically operated, but cutters comprising knife blades or ultrasonic cutters may be similarly configured and constructed.

Shaft 1404 carries and provides operating power for cutter 1400, for example, by an electrical cable including wire 1506 shown in FIG. 15, extending through shaft 1404 to a conventional diathermy system (not shown), or other suitable current supply. Shaft 1404 and/or wire 1506 are suitably electrically insulated. A suitable on-off control (not shown) is generally part of the diathermy device, but a separate on-off control may be included in the hand-piece.

The exemplary embodiment illustrated in FIGS. 14 and 15 is a unipolar system including a single wire. Optionally, however, bipolar systems may be used, in which case a neutral wire (not shown) may be contained in shaft 1404 in addition to the active wire, or in a separate shaft.

Shaft 1404 may be firmly connected, for example, by a suitable adhesive, to the outside surface 1410 of dilation device 1408. Optionally, a pocket (not shown) may be provided on outside surface 1410 to receive shaft 1404. A circumferential cut for receiving implant 1402 may be made with this embodiment by rotation of dilation device 1408, for example, on delivery shaft 1412.

Shaft 1406 carries and releases implant 1402, and optionally inserts it into the cut during or after it has been performed. Optionally and desirably, a sheath as described above surrounds the cutter 1400, implant 1402, and dilation device 1408 during delivery. In FIG. 14, the sheath has been removed for clarity, and cutter 1400 is in its operative position. As will be appreciated, after delivery to the implant site, the sheath will be removed, and implant 1402 and dilation device 1408 can assume their respective expanded conditions. Shaft 1404 itself may be attached to the outer surface 1410 of dilation device 1408, in which case, rotation of delivery device shaft 1412 by the surgeon to perform the cut.

Cutter 1400 may be positioned for operation by extending it out of shaft 1404 on a rod, or the like inside shaft 1404 connected to the cutter. Alternatively, if power wire 1506 is sufficiently rigid, it can be used to extend cutter 1400. As a further exemplary alternative, if cutter 1400 is surrounded by the sheath during delivery, it can be positioned so it lies flat against the dilation device 1408, until rotated to a radial orientation by the above-mentioned control rod. Optionally, if cutter 1400 is configured to lie against dilation device 1408 during deliver, it may be suitable connected to shaft 1404 and positioned for operation by rotation of shaft 1404. In such an embodiment, shaft 1404 may be rotatably received in the above-mentioned pocket on the surface 1410 of dilation device 1408, with the pocket being sufficiently rigid to retain shaft 1404 during the cutting operation.

Referring to FIG. 15, a T-shaped cutter 1500 is comprised of a cutting head 1502 that extends generally longitudinally relative to the urethra, and a cutter shaft 1504 which terminates in wire 1506. Cutter 1500 may be placed in its operative position as described in connection with FIG. 14.

Optionally, as further illustrated in FIG. 15, in some embodiments, the leading edges of blade 1502 and stem 1504 may be formed with sharp edges 1510 and 1512. This may improve the cutting performance and may reduce damage to the surrounding tissue. Optionally, the trailing parts 1508 of blade 1502 and 1514 of stem 1504 are coated by a polyxylylene polymer, for example, Parylene,® a fluoropolymer, for example, Teflon®, or other material having dielectric properties or other suitable material that provides sufficient electrical isolation. In that case, only the leading edges 1510 and 1512, which form the cut are un-coated. This may enable the electrical power required for operation to be reduced, without reduction of the cutting performance.

In some embodiments, electrical current is provided continuously during cutting. Optionally, current is provided intermittently. This also may reduce power consumption, by permitting the cut to be made by a combination of electrical and mechanical operation, utilizing sharp edge 1510.

Electric current may be provided at frequencies ranging from about 200 KHz-3.3 MHz at output power level in the range of about 5 w to about 400 w.

Power may be provided either in a pure cutting mode (continuous sinusoidal waveform) or pure coagulation mode (interrupted waveform) or blended modes that modify the degree of the duty cycles, as is known to those in the art.

Duty cycles may range from about 6% to 100%, or with lesser or intermediate duty cycles. The on-off repetition rate can range from about 120 Hz to about 20 KHz or lesser, or greater or intermediate repletion rates.

It will be appreciated that control of the depth of the cut will depend on the geometry, size, and location of the cutter, and the degree to which the urethra is expanded by the dilation device. Therefore, in the exemplary embodiments described herein, the dilation device action plays an important in achieving depth control. The dilation device should therefore be designed to expand the surrounding tissue substantially uniformly, so that the stretched urethra is substantially circular. In way, the distance between the dilation device surface 1410 and the upper part/edge of the cutter 1400 provides a substantially uniform cutting depth.

For example, in configurations such as illustrated in FIGS. 14 and 15, with cutter 1400 mounted on the surface 1410 of the dilation device 1408, the depth of the cut will be determined by the height of the cutter (or the distance between surface 1410 and the upper part/edge of the cutter 1400). As will be understood, in such configurations, the cut will be performed by rotation of the dilation device. Taking these factors into consideration, in an exemplary arrangement, the depth of the cut may be in the range of about 2 mm to about 5 mm, or with larger or smaller depths. It will be understood that cutting depth depends largely on the prostate geometry which limits the maximal depth.

FIGS. 16A-16D illustrate an embodiment of a cutter 1600, for example, electrically operated, comprised of a cutting head 1602 and a stem 1604 configured in the manner of cutter 900e (FIG. 9E). Cutter 1600 is carried in a sleeve 1606 attached to the outside surface 1608 of a dilation device 1610, for example, by an adhesive, either directly to the surface, or optionally in a fold or pocket (not shown) formed on the surface. Shaft 1606 may extend out through the main delivery device shaft, or may be separate and extend directly through the working channel.

As in the embodiment described in connection with FIGS. 14 and 15, an extension of stem 1604 shown at 1612 in FIG. 16D, passes through sleeve 1606 and connects to a diathermy machine. FIG. 16A shows cutter 1600 in its fully retracted delivery position, and FIG. 16D shows cutter 1600 in its fully extended operating position. FIGS. 16B and 16C show cutter 1600 in two intermediate positions between the fully retracted and fully extended positions. In the illustrated embodiment, cutter 1600 is pushed out from sleeve 1606 for operation and pulled back for delivery or removal by cutter extension 1612.

In an un-illustrated embodiment, a sleeve within which the cutter is delivered may be separate from the dilation device.

FIG. 16E shows another arrangement for a cutter 1622 carried by a sleeve 1624 inside a dilation device 1626. Here, sleeve 1624 terminates at its distal end 1628 in a port 1630 that is sealed from the inside of dilation device 1626 to provide an opening for cutter 1622, but does not interfere with expansion of the dilation device.

Figure 16H:
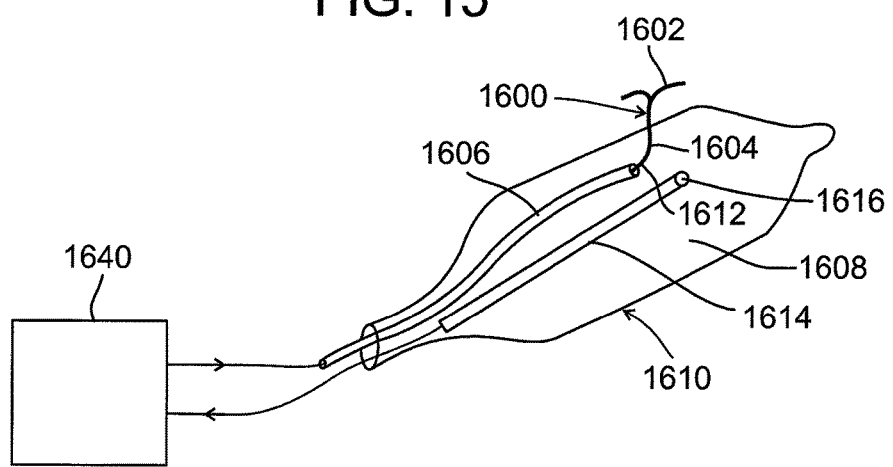
Figure 16F:
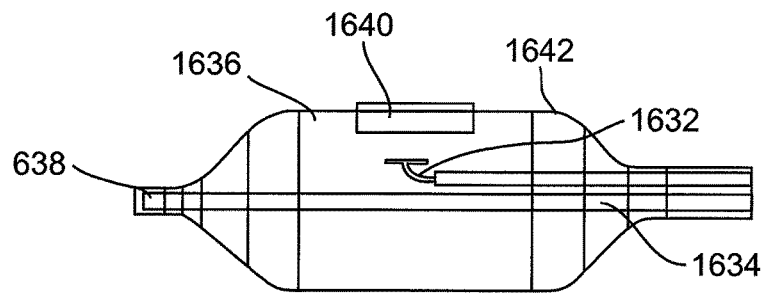
Figure 16G:
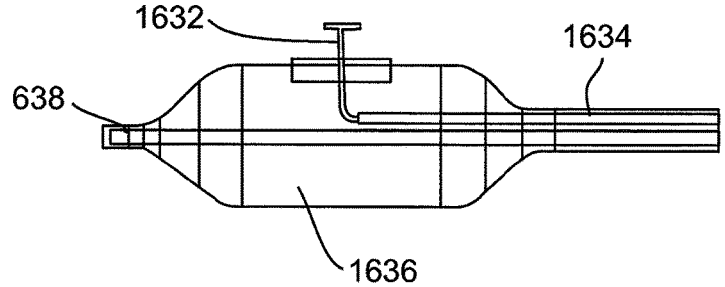

FIGS. 16F and 16G show another arrangement for a cutter 1632 carried by a sleeve 1634 inside a dilation device 1636. Here, a sleeve 1634 is located inside dilation device 1608 but is attached to the delivery device central shaft 1638. Cutter 1632 is configured to penetrate a self-sealing patch 1640 on the outer surface 1642 of dilation device 1636.

FIGS. 16F and 16G show cutter 1632 in its retracted and extended positions, respectively, Also, while self-sealing patch 1640 is shown on the outer surface 1642 of dilation device 1636, it may alternatively be mounted on the inner surface. Optionally, separate patches may be mounted on the inside and the outside of the dilation device.

As mentioned above, both mono-polar (unipolar) and bipolar systems may be used. An exemplary bipolar system is shown schematically in FIG. 16H, in which wire 1612 is the active wire, and a separate suitably insulated wire 1614 provides the neutral. The uninsulated tip 1616 of wire 1614 is the neutral pole, which closes the current path to the cutter 1600 through the prostate tissue.

The active and neutral wires may be provided in a single shaft, or optionally, in two separate shafts, and are connected at their outer ends to a diathermy machine 1640.

In a unipolar system, wire 1612 may be the active wire. The current return may optionally be provided by a ground plate which is coupled to the body of the patient.

Figure 17A:
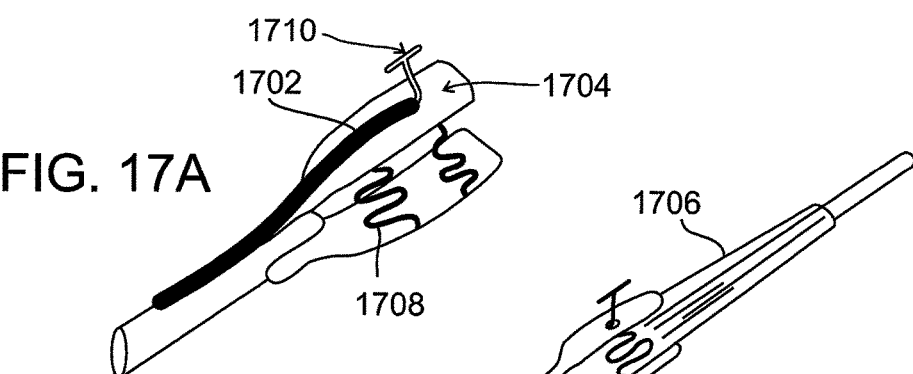
FIGS. 17A-17C are schematic illustrations of a cage configured for delivery of a cutter according to some embodiments of the invention.
Figure 17B:
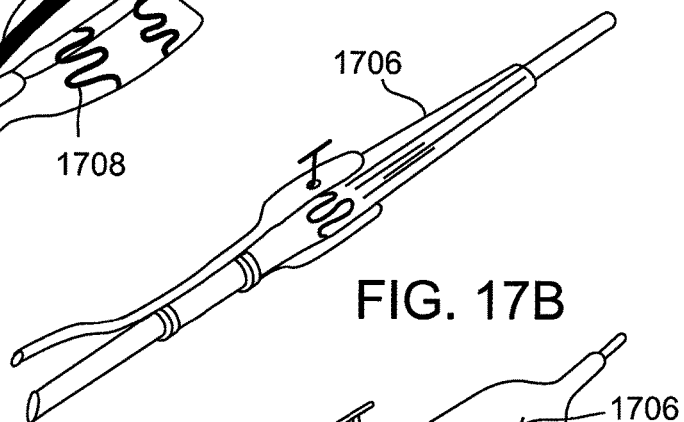
Figure 17C:
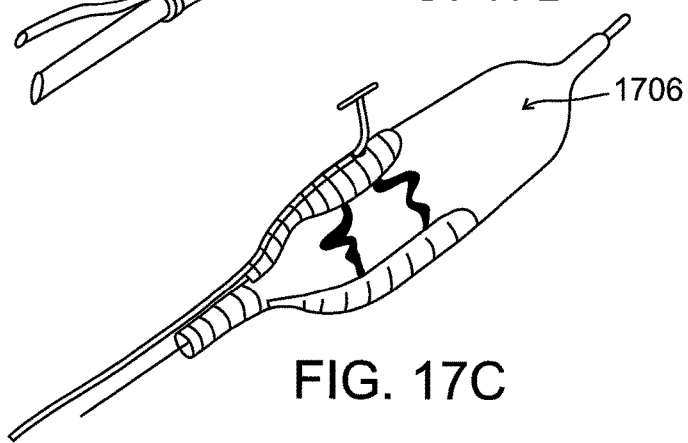

FIGS. 17A-17C illustrate another embodiment of an arrangement for delivering a cutter which is not carried on or in the dilation device. In this embodiment, the cutter 1700 is carried in a sleeve 1702 coupled to a separate cage 1704 that may be folded and positioned for delivery around unexpanded dilation device 1706 as in FIG. 17B. Cage 1704 is optionally formed of Nitinol, stainless steel or other biocompatible metal or a biocompatible polymer, for example, Teflon. Folded cage 1704 is configured to be opened by expansion of dilation device 1706, as shown in FIG. 17C, or may be self-expanding, for example, by action of springs 1708, when a surrounding sheath is withdrawn. In some embodiments the cage is rotated by rotation of the expanded dilation device 1706 on the delivery device main shaft (not shown). Alternatively, cage 1702 may be rotated on a separate shaft while dilation device 1706 remains fixed.

Figure 18:
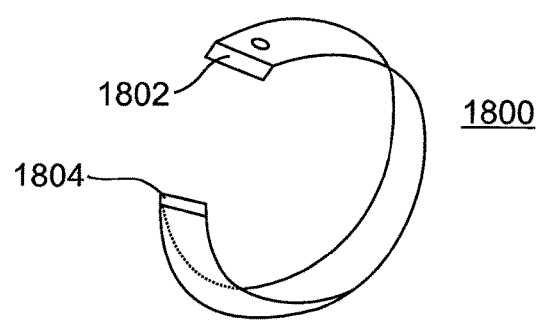
FIG. 18 is an illustration of an implant which performs all or a part of an implant-receiving cut according to some embodiments of the invention.

As described above, in some embodiments a cutter and the implant itself function together to perform the implant-receiving cut. Conversely, in some embodiments the implant is configured so that it alone serves as an electric cutting element. Such an embodiment is illustrated in FIG. 18, in which an implant 1800 includes a sharp leading edge 1802. Except for edge 1802, implant 1800 is coated with a polyxylylene polymer or similar polymer that provides dielectric isolation. The cutting edge 1802 is not coated. Current enters the implant at its trailing edge 1804, for example, through a metallic part of a suitable release mechanism, but because passes out through un-coated leading edge 1802 to heat the tissue and perform the cut.

As a further option, leading edge 1802 can perform mechanical cutting or combined mechanical and electrical cutting as described above in connection with FIG. 15.

In some situations, for example, where an enlarged prostate affects an extended portion of the urethra, it may be desirable in install multiple implants. For that purpose, the delivery system is configured to deliver multiple implants simultaneously, for example, 2-5 or more, as illustrated in embodiment of FIG. 19. Here, a dilation device 1900 carries three implants 1902, 1904, and 1906. The implants themselves may be as illustrated in FIG. 18 with sharp leading edges 1802. The cuts may be performed electrically, mechanically or by a combination of electrical and mechanical action.

Figure 19:
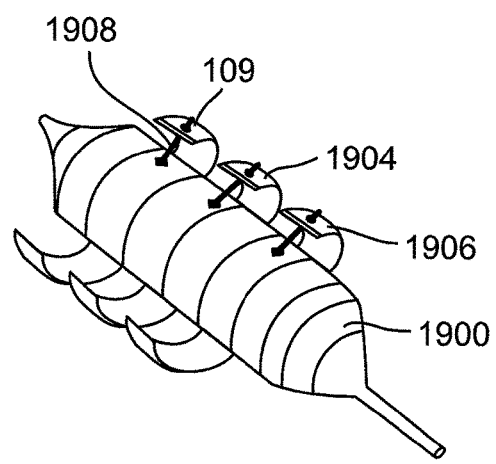
FIG. 19 illustrates a dilation device carrying multiple implants according to some embodiments of the invention.

Advantageously, the embodiment of FIG. 19 is configured so that all the cuts may be formed at one time, and to release all the implants simultaneously for insertion, either during or after performance of the cut. For that purpose, separate release mechanisms, for example, as illustrated in FIG. 17, may be provided under control of a single control element (not shown) extending out for operation by the surgeon.

As in other embodiments described, the cuts may be formed solely by the sharp leading edges of the implants, or in combination mechanical cutters.

Figure 20A:
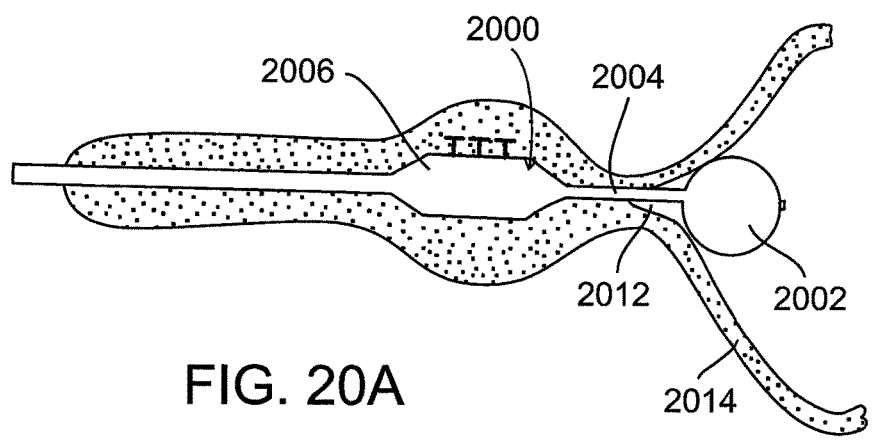
FIGS. 20A and 20B illustrate some ways of sealing the implant-receiving incision according to some embodiments of the invention.
Figure 20B:
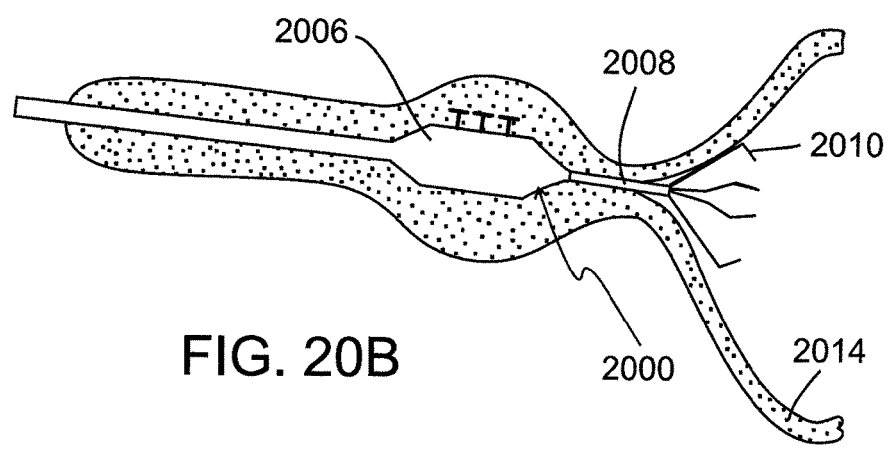

FIGS. 20A and 20B illustrate a feature of particular use in multiple-implant embodiments, but also useful when a single implant is being delivered. Here, the delivery/implantation unit 2000 includes a fixation or anchoring element at its distal end. FIG. 20A shows a fixation element in the form of a balloon 2002 positioned in the bladder 2014 and configured to be inflated through a fluid path 2004 extending from a dilation device 2006. Alternatively, as shown in FIG. 20B, the anchoring element can be formed of a number of resilient fingers 2010 carried by an extension 2008 of the delivery device main shaft. Other suitable anchoring arrangements may also be used.

The fixation elements of FIGS. 20A and 20B are expanded in bladder 2014 in order to prevent movement of delivery/implantation unit 2000 during the implantation procedure. This may facilitate positioning the multiple implants an accurate distance from the bladder neck 2012. In addition, the fixation element can help prevent the delivery system from moving during the procedure for single or multiple implantations.

In some embodiments, it may further be desirable to form a splice at the two sides of the implant-receiving incision to improve the wound healing performance. Several options for this are possible, for example, biocompatible glue may be applied by the implant itself or by a suitable applicator inserted through the main shaft or the cystoscope.

Figure 21A:
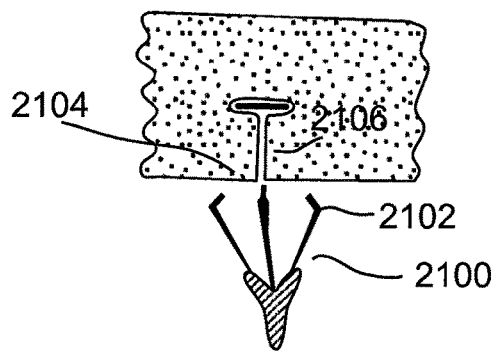
FIGS. 21A-21C illustrate closure of the implant-receiving incision according to some embodiments of the invention.
Figure 21B:
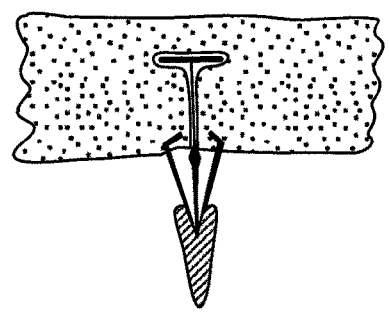

FIGS. 21A and 21B illustrate an alternative way to form a splice using a suitably sized removable clamp 2100 inserted through the working channel as previously described. Clamp 2100 is illustrated in an open configuration in FIG. 21A. As illustrated in FIG. 21B, clamp 2100 may be closed, for example, by a pull wire or suitable rod, to move the sharp ends 2102 of clamp 2100 toward each other and into the prostate wall to pull the edges 2104 of the cut 2106 together. After a suitable time has elapsed for healing, clamp 2100 may be removed.

Figure 21C:
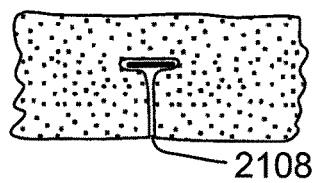

FIG. 21C illustrates an alternative embodiment in which a suture 2108 is used to close the edge 2110 of the cut 2112. Clamping or suturing may be performed in any suitable desired manner known to surgeons. The splice can be performed during the cutting process, for example if the implant is deployed while the cut is being made. Alternatively, splicing may be performed after the implant has been deployed.

Detailed Description of Exemplary Method Embodiments

Figure 22:
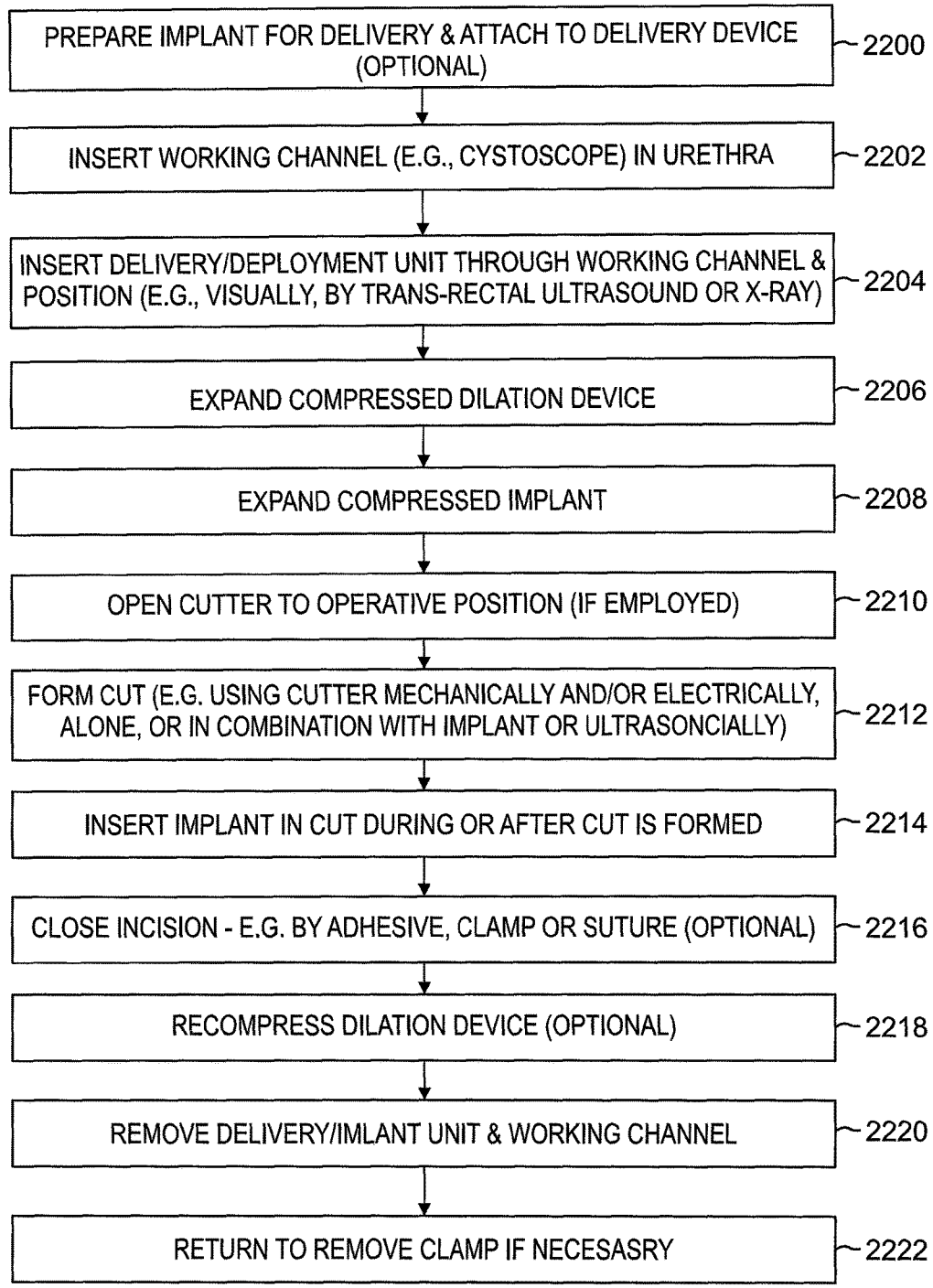
FIG. 22 is a block diagram that illustrates details of exemplary implantation methods according to some embodiments of the invention.

Referring to FIG. 22, an exemplary method of deployment of implants according to some embodiments of the invention is shown in detail in flow chart form.

At 2200, an implant is prepared for delivery. This may be done by configuring it compactly, for example by folding, or forming it into a roll, or by inserting it and one or more other components of the delivery system in a sheath, to facilitate delivery and to minimize risk of damage to the urethra, Preparation may optionally also include releasably attaching the implant to a delivery device. Optionally, preparation may take place as a preliminary to the medical procedure, or an implant already attached to part of a delivery system may be obtained as part of a kit (which is partially or completely disposable) optionally including the implant, the cutter and the urethral dilation device. When in kit form, the preassembled parts are attached to the surgeons control unit, and if necessary to an ultrasonic driver or a diathermy unit At 2202, a working channel provided, for example, by a cystoscope, is inserted through the urethra. Note that elements 2100 and 2102 may be performed in reverse order if the implant is attached to its delivery device as part of the medical procedure, but the order stated may be more desirable since the actual performance of the implantation may be less time consuming.

At 2204, the delivery/deployment unit is inserted through the working channel to the desired location. Positioning may be accomplished, for example, by direct visual observation through the cystoscope, by a dedicated optical device, by trans-rectal ultrasound, radiographically, or by other imaging modality.

At 2206, the dilation device, which has been inserted in a compressed condition, is expanded. This may be done by inflation for a dilation device in the form of one or more balloons, or optionally, the dilation device may be self-expanding when released from a delivery sheath due to elastic properties of the material.

At 2208, the implant, which is also delivered in a compressed configuration in some embodiments of the invention, is expanded for deployment. As in the case of the dilation device, a sheath or other compression device which maintains the implant in a compressed condition during delivery is opened or withdrawn to restore the implant to at least a partially relaxed condition. Optionally, the dilation device and the implant are delivered in the same sheath, and may be decompressed at the same time when the sheath is opened or withdrawn.

At 2210, the cutter, which in some embodiments is delivered in a retracted or folded condition, is opened to its operative configuration. In some embodiments of the invention, the implant, the cutter and the dilation device are delivered in one unit. Alternatively, if they are delivered separately, the order of delivery is optional.

At, 2212, the cutter is operated to form a cut for receiving the implant. The cut may, for example, be a groove or a narrow slit, depending on the width of a strip implant, (or effective diameter of a wire implant). The cut may be made after the urethra has been dilated, or while dilation is in progress. The cut may be made mechanically, for example by a sharp blade, or thermally, for example, by ultrasound or electrically. Optionally, the implant itself can form the cut, either mechanically, or electrically, either alone, or in cooperation with the cutter.

At 2214, the implant is deployed in the cut. The implant may be deployed while the cut is being made, for example, if the implant itself performs the cutting, or is delivered attached to the cutter. Optionally, the implant may be inserted after the cut is completed, in which case, the order of method elements 2212 and 2214 may be reversed Optionally, at 2116, the edges of implant-receiving incision may be closed to promote healing. This may be done by application of an adhesive, for example, by the implant itself, or by a separate applicator. Optionally, the incision may be closed by a clamp or a suture. Choice of the closure mechanism, and whether to provide any closure, is at the discretion of the surgeon.

Optionally, at 2218, the dilation device is recompressed, for example by deflation. Optionally it may be removed without recompression. At 2220, the delivery device and the and the working channel are withdrawn.

Finally, with the procedure complete, at 2222, if a clamp has been used to close the incision, after a suitable time for healing, a cystoscope is reinserted to provide a working channel and the clamp is withdrawn. As will be understood, if a suture is used as the closure device, it may be biodegradable, and a subsequent removal step would not be necessary.

If the length of the obstruction is such that more than one implant is needed, the delivery device is prepared with the required number of implants at 2200. Then at 2212, multiple cuts are formed, optionally, simultaneously. Advantageously, the implants themselves may form the cuts, either mechanically, or electrically, or by a combination of both. Optionally, if the implants form or participate in forming the cuts, they are inserted in the cuts while the cuts are being made, again, optionally, simultaneously. For multiple implants, it may be desirable to anchor the delivery device in the bladder after 2208.

General Information and Definitions

For general reference, certain terms used in the description are to be understood as having the following meanings:

The term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as limiting.

What is claimed is:

1. A method of treatment of an intra-body lumen comprising:
    inserting an elongate implant formed of a resilient material into a lumen to be treated, wherein the lumen is a constricted portion of a urethra; and
    forming an arcuate cut in an inner surface of a prostate tissue surrounding the constricted portion, said arcuate cut extending in a circumferential extent in the inner surface for a length sufficient to circumferentially receive a full length of said implant when deployed in said cut, said cut radially open to said lumen over said sufficient length, said cut defines two tissue flaps on either side thereof over said sufficient length; and
    deploying the implant in the cut such that the implant extends along the cut.

2. The method according to claim 1, further including delivering the implant to the area to be treated in a compressed condition, and deploying the implant in the cut in at least a partially uncompressed condition.

3. The method according to claim 1, wherein the cut is formed by a cutter delivered to the area to be treated, or by the implant, or by cooperation of a cutter and the implant.

4. The method according to claim 1, wherein the cut is formed by a sharp edge of a cutter and/or the implant, and/or by application of electrical current delivered from an electrical source or by a piezoelectric transducer to the area being cut.

5. The method according to claim 4, wherein energy is provided continuously or intermittently during the cut formation.

6. The method according to claim 1, further including closing the implant-receiving cut after deployment of the implant by application of an adhesive, or by a clamp, or by a suture.

7. The method according to claim 1, wherein the implant is configured as one of:
(a) a flat-surfaced open or closed ring, having at least one of the following:
(i) with or without holes in the surfaces;
(ii) with or without protrusions on a radially outer surface or on the edges; or
(b) a closed or open ring formed of a wire.

8. The method according to claim 7, wherein the open ring is C-shaped.

9. A method according to claim 1, wherein the cut is formed by rotating a cutter around an inner surface of the tissue surrounding an area of the lumen requiring treatment.

10. A method according to claim 1, further comprising removing the implant after a predetermined time, or wherein the implant is formed of a material that is biodegradable.

11. A method according to claim 1, wherein said cut is formed by a cutter delivered to the area to be treated, said cutter is different from said implant.

12. A method according to claim 1, wherein said cut is in the form of a T-shaped cross-section.

13. A method according to claim 1, wherein said cut is less than a complete circle.

14. A method according to claim 1, wherein said inserting includes inserting the implant in at least a partially compressed state, wherein the implant is configured to apply a radially outward force in the cut to provide post-deployment dilation of the urethra.

15. A method according to claim 1, wherein deploying said implant comprises deploying the entire implant in the cut.

16. A method according to claim 1, further comprising closing the implant-receiving cut in the surface of the prostate tissue by pulling together edges of the cut prostate tissue.

17. A method according to claim 1, wherein said implant comprises curved leading edges configured to facilitate entry of said leading edges into the cut.

18. A method according to claim 1, wherein said arcuate cut is a complete circle in the inner surface of the prostate tissue surrounding the constricted area, and wherein said implant is deployed circumferentially into the complete circle in the inner surface of the prostate tissue.

19. A method according to claim 1, wherein said implant is deployed while the arcuate cut is being formed.

20. The method according to claim 1, further comprising expanding the lumen using a dilation device before and/or during formation of the cut.

21. The method according to claim 20, wherein the dilation device is a balloon and is expanded by inflation, or is a self-expanding device and is expanded by releasing it from a carrier in which it is delivered to the deployment site.

22. A method according to claim 1, further comprising anchoring a delivery/implantation unit for the implant during cutting and deployment of the implant.

23. The method according to claim 22, wherein the lumen is a urethra constricted by an enlarged prostate and the delivery/implantation unit is anchored by a balloon inserted into the bladder.

* * * * *